US009551967B2

(12) United States Patent
Takenaga et al.

(10) Patent No.: US 9,551,967 B2
(45) Date of Patent: Jan. 24, 2017

(54) SHEET DISCRIMINATOR AND IMAGE FORMING APPARATUS INCORPORATING THE SHEET DISCRIMINATOR

(71) Applicants: Noriaki Takenaga, Tokyo (JP); Tohru Matsumoto, Ibaraki (JP); Tetsuya Ofuchi, Kanagawa (JP); Takayuki Nishimura, Kanagawa (JP); Yukifumi Kobayashi, Kanagawa (JP); Hideyo Makino, Tokyo (JP); Satoshi Nakayama, Kanagawa (JP)

(72) Inventors: Noriaki Takenaga, Tokyo (JP); Tohru Matsumoto, Ibaraki (JP); Tetsuya Ofuchi, Kanagawa (JP); Takayuki Nishimura, Kanagawa (JP); Yukifumi Kobayashi, Kanagawa (JP); Hideyo Makino, Tokyo (JP); Satoshi Nakayama, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/681,274

(22) Filed: Apr. 8, 2015

(65) Prior Publication Data
US 2015/0293487 A1 Oct. 15, 2015

(30) Foreign Application Priority Data

Apr. 10, 2014 (JP) .................................. 2014-080785
Jul. 2, 2014 (JP) .................................. 2014-136498

(51) Int. Cl.
*G01N 21/55* (2014.01)
*G03G 15/00* (2006.01)
(Continued)

(52) U.S. Cl.
CPC ......... *G03G 15/5029* (2013.01); *G01B 5/0023* (2013.01); *G01B 5/24* (2013.01);
(Continued)

(58) Field of Classification Search
USPC ............... 356/445–448, 429–430, 625–640
See application file for complete search history.

(56) References Cited

U.S. PATENT DOCUMENTS 6,718,145 B2 * 4/2004 Ohta .................. G03G 15/5029
399/16
7,343,689 B2 * 3/2008 Kondo ............... G01B 11/0691
33/501.02
(Continued)

FOREIGN PATENT DOCUMENTS

JP 2007-233186 9/2007
JP 2012-208103 10/2012

OTHER PUBLICATIONS

U.S. Appl. No. 14/557,603, filed Dec. 2, 2014.
U.S. Appl. No. 14/582,261, filed Dec. 24, 2014.

*Primary Examiner* — Tri T Ton
(74) *Attorney, Agent, or Firm* — Harness, Dickey & Pierce, P.L.C.

(57) ABSTRACT

A sheet discriminator, which can be included in an image forming apparatus, includes an optical information detector, a sheet distinguisher, and a sheet thickness detector. The optical information detector includes a light emitter to emit light to a recording medium and a light receiver to receive the light and detects information of the recording medium. The sheet distinguisher distinguishes a type of the recording medium based on the information detected by the optical information detector. The sheet thickness detector includes a displacement gauge to sandwich the recording medium with an opposing member disposed facing the displacement gauge and to move from an initial position thereof and a displacement detector to detect an amount of displacement of the displacement gauge. The sheet thickness detector detects a thickness of the recording medium based on detection results obtained by the displacement detector.

20 Claims, 22 Drawing Sheets

(51) Int. Cl.
  *G01N 21/59* (2006.01)
  *G01B 5/00* (2006.01)
  *G01B 5/24* (2006.01)
  *G01N 21/21* (2006.01)
  *G01N 21/47* (2006.01)
(52) U.S. Cl.
  CPC ............ *G01N 21/55* (2013.01); *G01N 21/59* (2013.01); *G01N 21/21* (2013.01); *G01N 21/474* (2013.01); *G01N 2021/556* (2013.01); *G01N 2021/558* (2013.01); *G01N 2201/0612* (2013.01); *G01N 2201/0683* (2013.01); *G03G 2215/00738* (2013.01); *G03G 2215/00751* (2013.01)

(56) References Cited

U.S. PATENT DOCUMENTS

2006/0020365 A1* 1/2006 Takeda ............... G03G 15/6591
  700/226
2013/0194573 A1 8/2013 Ohba et al.

* cited by examiner

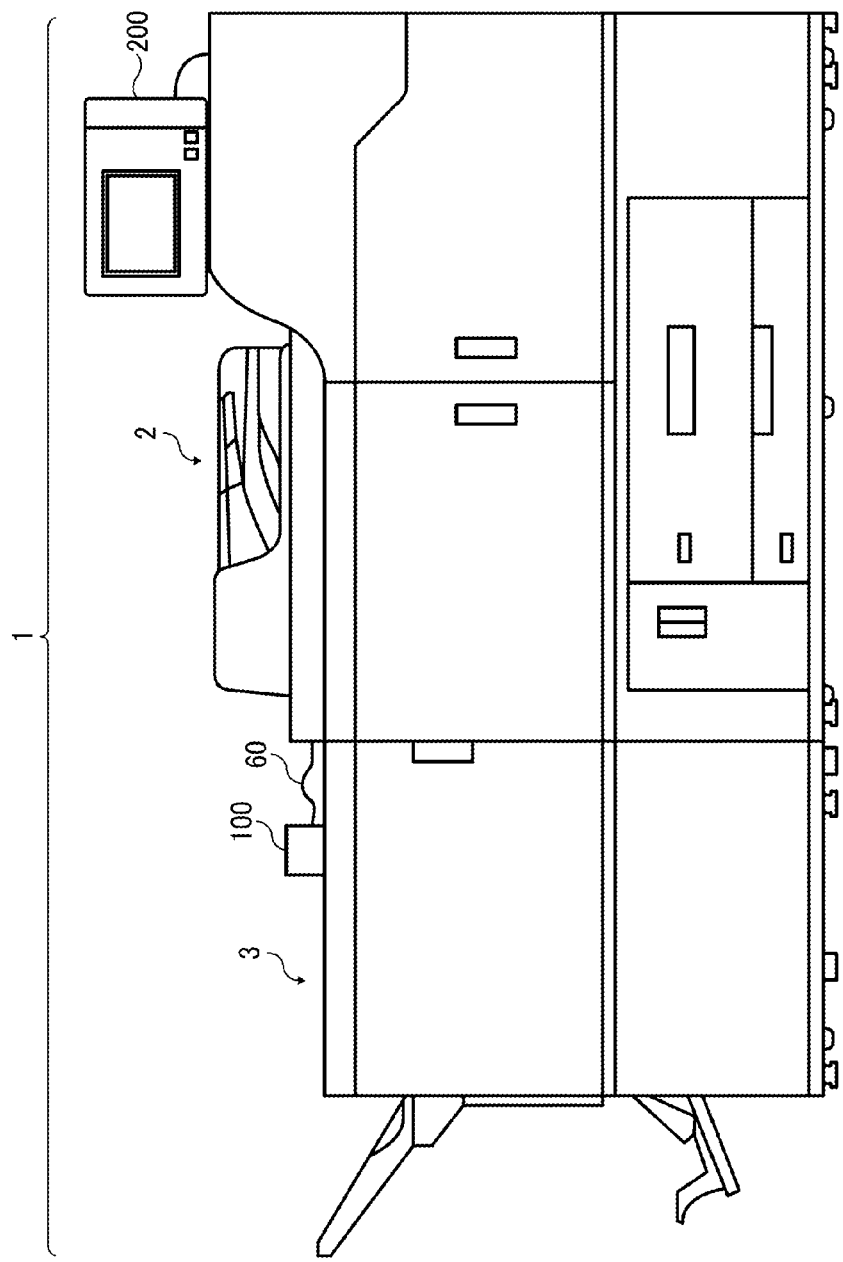

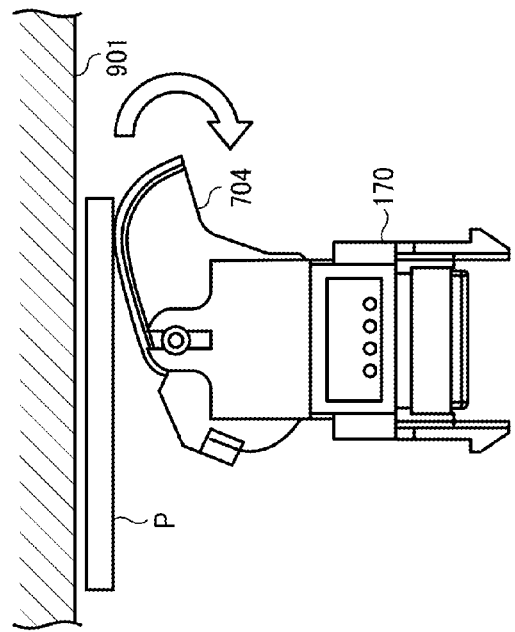
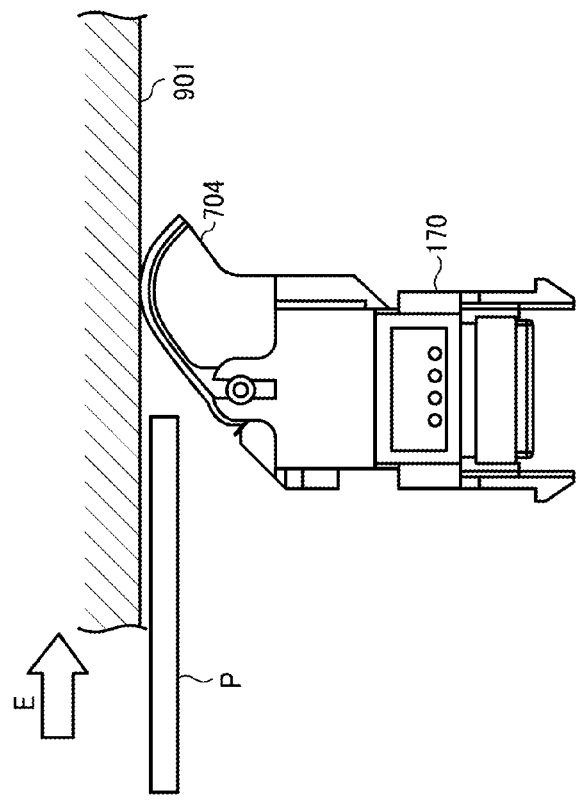

SHEET DISCRIMINATOR AND IMAGE FORMING APPARATUS INCORPORATING THE SHEET DISCRIMINATOR

CROSS-REFERENCE TO RELATED APPLICATIONS

This patent application is based on and claims priority pursuant to 35 U.S.C. §119(a) to Japanese Patent Application Nos. 2014-080785, filed on Apr. 10, 2014, and 2014-136498, filed on Jul. 2, 2014, in the Japan Patent Office, the entire disclosure of each of which is hereby incorporated by reference herein.

BACKGROUND

Technical Field

This disclosure relates to a sheet discriminator to discriminate sheet types, and an image forming apparatus including the sheet discriminator.

Related Art

In known image forming processes, to achieve higher printing quality, an image forming apparatus automatically discriminates sheet types and sets image forming conditions according to the detected sheet type.

An example of an image forming apparatus shows a configuration in which a sheet discriminator is disposed inside the image forming apparatus to discriminate information of a sheet being conveyed in a sheet conveying path.

This sheet discriminator includes an optical sensor that has a light emitting element and a light receiving element therein to function as a sheet information detector to detect information of a sheet. The light emitting element of the sheet information detector emits light to a surface of a sheet. Among the light emitted by the light emitting element, the light reflected on the surface of the sheet is received by a reflection light receiving element that is disposed at a position that can receive the reflected light and the light transmitted through the surface of the sheet is received by a transmission light receiving element that is received at a position that can receive the transmitted light.

Specifically, the sheet information detector causes the light emitting element to emit light to a sheet that is conveyed via a sheet conveying path and causes the reflection light receiving element to receive the light reflected on the sheet and the transmission light receiving element to receive the light transmitted through the sheet, so that the sheet information detector can detect sheet information based on optical information including a light amount of the received light.

Accordingly, based on the sheet information thus detected by the sheet information detector, a controller that functions as a sheet distinguisher to distinguish the sheet types, the image forming apparatus sets the image forming conditions according to the sheet type.

The sheet information detected by the sheet information detector includes glossiness of the sheet based on the reflected light received by the reflection light receiving element, thickness of the sheet based on the transmitted light received by the transmission light receiving element, and so forth. Based on the sheet information detected as described above, a controller that is a sheet distinguisher distinguishes a type of the sheet so as to set image forming conditions according to the respective types of the sheets.

SUMMARY

At least one aspect of this disclosure provides a sheet discriminator including an optical information detector, a sheet distinguisher, and a sheet thickness detector. The optical information detector includes a light emitter to emit light to a surface of a recording medium and a light receiver to receive the light emitted by the light emitter and detects information of the recording medium. The sheet distinguisher distinguishes a type of the recording medium based on the information detected by the optical information detector. The sheet thickness detector includes a displacement gauge and a displacement detector. The displacement gauge sandwiches the recording medium with an opposing member disposed facing the displacement gauge and moves from an initial position at which the displacement gauge stays when no recording medium is sandwiched with the opposing member. The displacement detector detects an amount of displacement of the displacement gauge. The sheet thickness detector detects a thickness of the recording medium based on detection results obtained by the displacement detector.

Further, at least one aspect of this disclosure provides an image forming apparatus including an apparatus body, the above-identified sheet discriminator disposed outside the apparatus body, and an image forming part to form an image on the recording medium.

BRIEF DESCRIPTION OF THE SEVERAL VIEWS OF THE DRAWINGS

FIG. 16 is a diagram illustrating a configuration of an image forming system according to an example of this disclosure;

FIG. 24A is a diagram illustrating an encoder feeler of a sheet thickness sensor of the sheet discriminator before the sheet is inserted;

FIG. 24B is a diagram illustrating the encoder feeler after the sheet is inserted;

DETAILED DESCRIPTION

Figure 1:
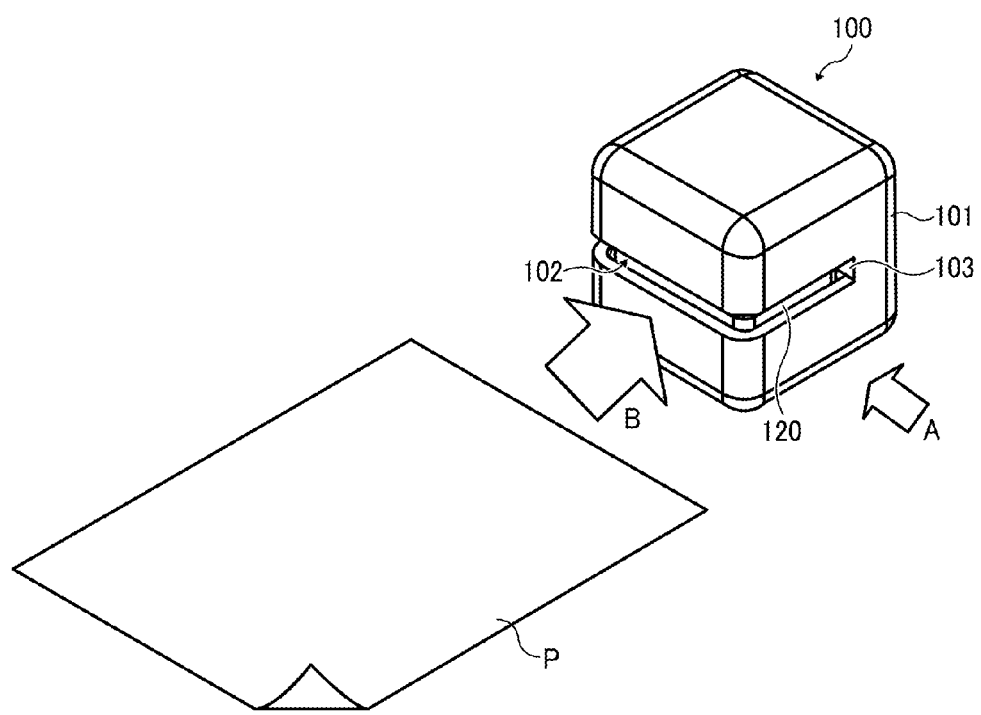
FIG. 1 is a diagram illustrating a sheet discriminator according to an example of this disclosure.

It will be understood that if an element or layer is referred to as being "on", "against", "connected to" or "coupled to" another element or layer, then it can be directly on, against, connected or coupled to the other element or layer, or intervening elements or layers may be present. In contrast, if an element is referred to as being "directly on", "directly connected to" or "directly coupled to" another element or layer, then there are no intervening elements or layers present. Like numbers referred to like elements throughout. As used herein, the term "and/or" includes any and all combinations of one or more of the associated listed items.

Spatially relative terms, such as "beneath", "below", "lower", "above", "upper" and the like may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements describes as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors herein interpreted accordingly.

Although the terms first, second, etc. may be used herein to describe various elements, components, regions, layers and/or sections, it should be understood that these elements, components, regions, layer and/or sections should not be limited by these terms. These terms are used to distinguish one element, component, region, layer or section from another region, layer or section. Thus, a first element, component, region, layer or section discussed below could be termed a second element, component, region, layer or section without departing from the teachings of the present disclosure.

The terminology used herein is for describing particular embodiments and examples and is not intended to be limiting of exemplary embodiments of this disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Descriptions are given, with reference to the accompanying drawings, of examples, exemplary embodiments, modification of exemplary embodiments, etc., of an image forming apparatus according to exemplary embodiments of this disclosure. Elements having the same functions and shapes are denoted by the same reference numerals throughout the specification and redundant descriptions are omitted. Elements that do not demand descriptions may be omitted from the drawings as a matter of convenience. Reference numerals of elements extracted from the patent publications are in parentheses so as to be distinguished from those of exemplary embodiments of this disclosure.

This disclosure is applicable to any image forming apparatus, and is implemented in the most effective manner in an electrophotographic image forming apparatus.

In describing preferred embodiments illustrated in the drawings, specific terminology is employed for the sake of clarity. However, the disclosure of this disclosure is not intended to be limited to the specific terminology so selected and it is to be understood that each specific element includes any and all technical equivalents that have the same function, operate in a similar manner, and achieve a similar result.

Referring now to the drawings, wherein like reference numerals designate identical or corresponding parts throughout the several views, preferred embodiments of this disclosure are described.

Now, a description is given of a sheet discriminator 100 according to this disclosure with reference to FIGS. 1 through 26.

First, a description is given of a configuration of the sheet discriminator 100 according to an example of this disclosure with reference to FIGS. 1 through 15.

FIG. 1 is a diagram illustrating a configuration of the sheet discriminator 100.

The sheet discriminator 100 includes an external case 101. The external case 101 includes a sheet information detecting sensor 110, a sheet thickness detecting sensor 170, and a sheet loading table 120 therein. The sheet information detecting sensor 110 functions as an optical information detector to optically detect information to be used to discriminate the sheet P. The sheet thickness detecting sensor 170 functions as a sheet thickness detector to detect a thickness of the sheet P. The sheet loading table 120 functions as a sheet loading table on which the sheet P is located.

It is to be noted that the sheet information detecting sensor 110 and the sheet thickness detecting sensor 170 form an information detector 180 to detect information of the sheet P in the sheet discriminator 100.

Figure 3:
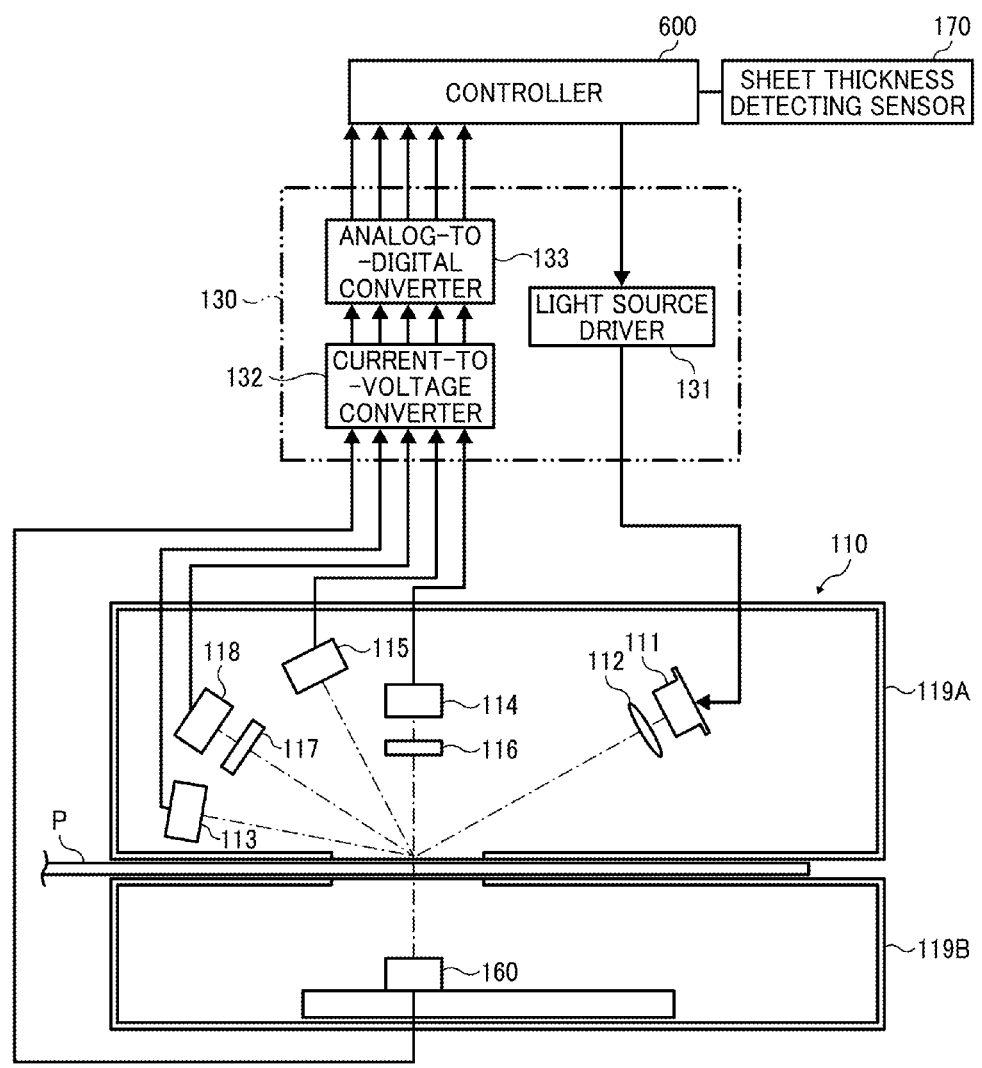
FIG. 3 is a diagram illustrating a configuration of an optical sensor and a processing device.

It is to be noted that the sheet information detecting sensor 110 and the sheet thickness detecting sensor 170 are connected via a controller 600 that functions as a sheet distinguisher (see FIG. 3). Based on whether the thickness of the sheet is detected by the sheet thickness detecting sensor 170 or not, the controller 600 controls start and stop of light emission of a light source 111 (see FIG. 3) of the sheet information detecting sensor 110 via a light emission processing unit 130 that functions as a light emission controller.

The external case 101 has sidewalls. An opening 102 is formed on one of the sidewalls of the external case 101. The sheet P is inserted into and removed from the opening 102 so that the sheet P is loaded on the sheet loading table 120. The sheet P is inserted into the opening 102 of the sheet discriminator 100 in a direction indicated by arrow B in FIG. 1 and pushed further until the sheet P contacts an end face 103 of the opening 102 or approaches the end face 103.

At this time, it is preferable that the operator grabs both left and right ends of the sheet P with respect to the direction B and inserts the sheet while checking that the sheet P has no deformation such as wrinkle or crease on the sheet P. It is to be noted that sheet insertion is not limited to the above-described way but is applicable with any way of sheet insertion even if the sheet P can be inserted into the opening 102 of the sheet discriminator 100 horizontally.

To discriminate a type of the sheet P, the operator inserts the sheet P into the external case 101 via the opening 102 while checking that there is no deformation such as curls on the sheet P held by the operator. Then, the operator loads the sheet P on the sheet loading table 120, so that the sheet information detecting sensor 110 detects information of the sheet P while the sheet P is loaded on the sheet loading table 120.

By so doing, the sheet information detecting sensor 110 does not detect deformed portions on the sheet P and detects correct sheet information, and therefore performance of accurate discrimination of sheet types is prevented from being degraded.

Figure 2A:
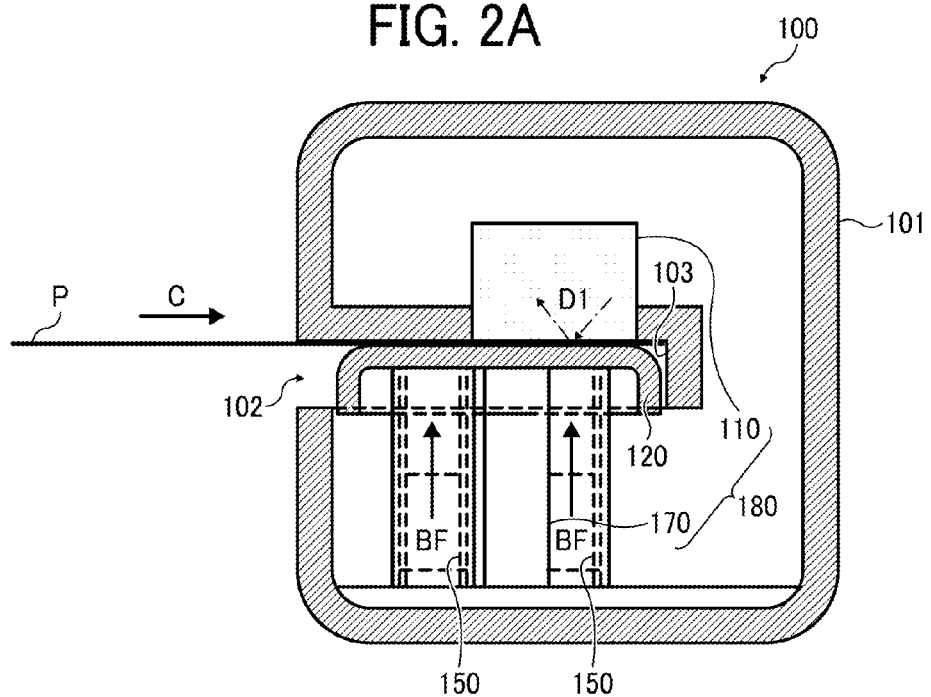
FIG. 2A is a cross sectional view illustrating the sheet discriminator when a sheet is inserted thereto through an opening.
Figure 2B:
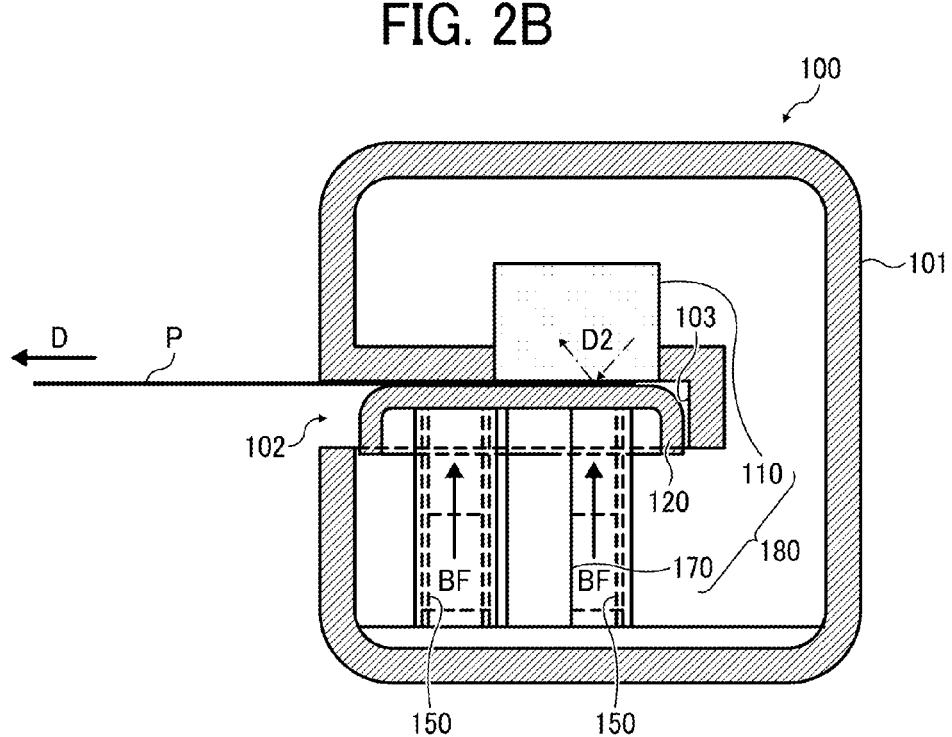
FIG. 2B is a cross sectional view illustrating the sheet discriminator when the sheet is pulled out from the opening of the sheet discriminator.

FIGS. 2A and 2B are cross sectional views of the sheet discriminator 100, viewed from a direction indicated by arrow A in FIG. 1. Specifically, FIG. 2A is a cross sectional view illustrating the sheet discriminator 100 when the sheet P is inserted thereto through the opening 102 of the sheet discriminator 100 and FIG. 2B is a cross sectional view illustrating the sheet discriminator 100 when the sheet P is pulled out from the opening 102 of the sheet discriminator 100.

It is to be noted that respective sensors such as the sheet information detecting sensor 110 and the sheet thickness detecting sensor 170 are drawn in a simplified way in FIGS. 2A and 2B.

The sheet information detecting sensor 110 is disposed at an upper part of an inside of the external case 101 of the sheet discriminator 100.

The sheet loading table 120 and the sheet thickness detecting sensor 170 are disposed at a lower art of the inside of the external case 101 of the sheet discriminator 100.

The sheet loading table 120 is disposed facing the sheet information detecting sensor 110 across a gap therebetween. The sheet thickness detecting sensor 170 is disposed upstream from a sheet information detectable position of the sheet information detecting sensor 110.

With this configuration, when the sheet P is inserted through the opening 102 to the sheet information detectable position so that the sheet information detecting sensor 110 can detect sheet information, the sheet thickness detecting sensor 170 can detect the thickness of the sheet P reliably. Accordingly, the sheet thickness detecting sensor 170 can detect the thickness of the sheet P more accurately, and accuracy in sheet discrimination can be more enhanced.

It is to be noted that, even though the sheet thickness detecting sensor 170 is disposed at the above-described position, the position to set the sheet thickness detecting sensor 170 is not limited thereto. For example, the sheet thickness detecting sensor 170 can be disposed in an upper part inside the external case 101 of the sheet discriminator 100 and aligned with the sheet information detecting sensor 110. The sheet thickness detecting sensor 170 can be disposed at any position where the sheet thickness detecting sensor 170 can detect the thickness of the sheet P that is inserted into the sheet discriminator 100 through the opening 102.

Further, biasing members 150 such as spring are disposed facing the sheet information detecting sensor 110 with the sheet loading table 120 interposed therebetween. The sheet loading table 120 is biased by the biasing members 150 in a direction indicated by arrows BF in FIGS. 2A and 2B, that is, toward the sheet information detecting sensor 110.

As illustrated in FIG. 3, the sheet information detecting sensor 110 includes a light source 111, a collimator lens 112, receivers 113, 114, 115, 118, and 160, polarizing filters 116 and 117, and dark boxes (camera obscuras) 119A and 119B to accommodate these optical units therein.

Each of the dark boxes 119A and 119B is a metal box such as an aluminum box, and anodic oxide coating with black dye on a surface thereof in order to reduce the impact of ambient light and stray light.

Figure 4:
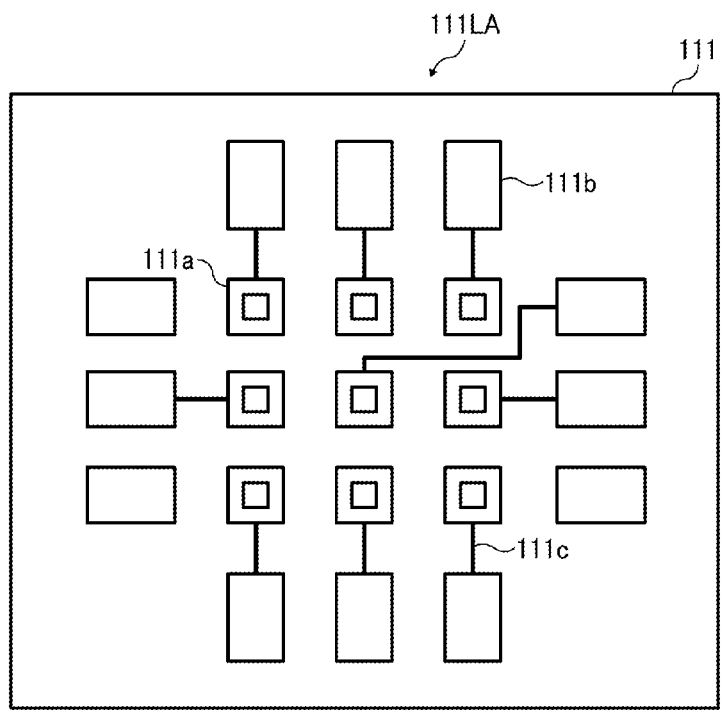
FIG. 4 is a diagram illustrating a structure of a vertical cavity surface emitting laser array (a VCSEL array)

The light source 111 functions as a light emitter and includes multiple light emitting elements 111a, which are vertical cavity surface emitting laser (VCSEL). Specifically, the light source 111 includes a VCSEL array 111LA. As illustrated in FIG. 4, the light source 111 of the sheet information detecting sensor 110 includes a two dimensional array with nine (9) light emitting elements 111a. The VCSEL array 111LA includes electrode pads 111b and wiring members 111c. Each wiring member 111c connects one of the multiple light emitting elements 111a with a corresponding one of the electrode pads 111b.

Figure 5:
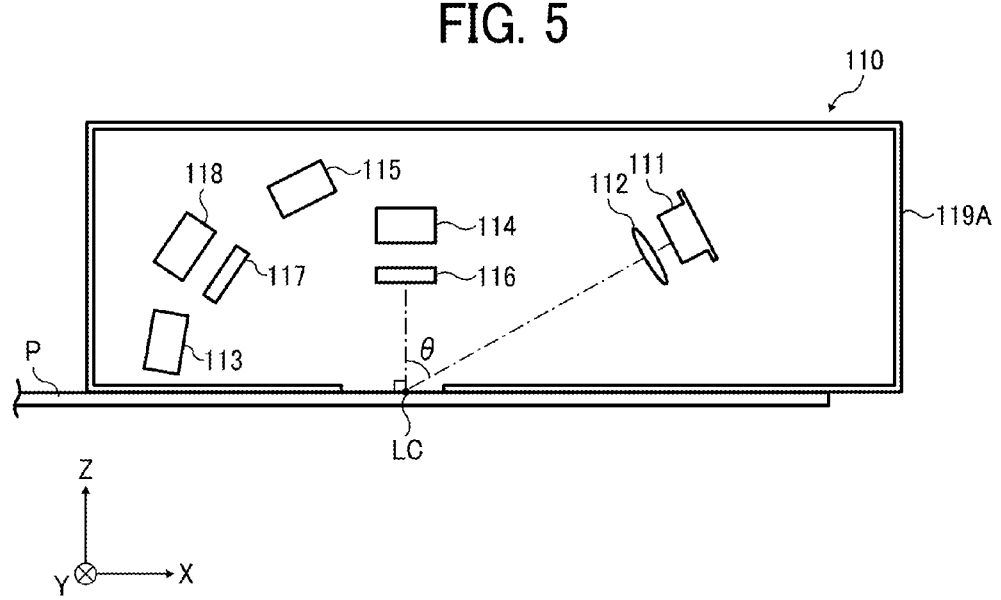
FIG. 5 is a diagram illustrating an incident angle of an irradiation light to the sheet.

The light source 111 is disposed such that linearly polarized light of S-polarized light to the sheet P is emitted. As illustrated in FIG. 5, an incidence angle θ of light from the light source 111 to the sheet P is 80 degrees. The light emission processing unit 130 turns on/off the light source 111.

The collimator lens 112 is disposed on a light path of light emitted from the light source 111 to make the light substantially parallel, which is hereinafter referred to as a substantially parallel light. The substantially parallel light passes through the collimator lens 112 then through an opening provided on the dark box 119A, and emits the light to the sheet P. It is to be noted that a center of a light emission region on a surface of the sheet P is hereinafter referred to as a "center of light emission (LC)" and the light passed through the collimator lens 112 is also referred to as an "irradiation light".

When the light enters onto a border surface of a medium, a surface that contains an incident light (an incoming radiation) and a normal line of a border surface standing at a light incident point. When the incident light includes multiple light beams, each light beam has the plane of incidence. Here, for convenience, the plane of incidence of light incoming to the center of light emission is referred to as a "plane of incidence" of the sheet P. Specifically, the plane of incidence of a sheet contains the center of light emission (LC) and is parallel to X and Z surfaces of the sheet P.

It is to be noted that terms "S-polarized light" and "P-polarized light" are used for not only the incident light to the sheet P but also a reflection light on the sheet P based on a polarization direction of the incident light to the sheet P for easy understanding of this technique. On the plane of incidence, a polarization direction identical to the incident light is referred to as "S-polarized light" and a polarization direction perpendicular to the incident light is referred to as "P-polarized light". In this example, the incident light is an S-polarized light.

The polarizing filter 116 is disposed on a +Z side of the center of light emission. The polarizing filter 116 is a polarizing filter that transmits the P-polarized light and blocks or reflects the S-polarized light. It is to be noted that a polarizing beam splitter that has the same functions as the polarizing filter 116 can be employed instead of the polarizing filter 116.

Figure 6:
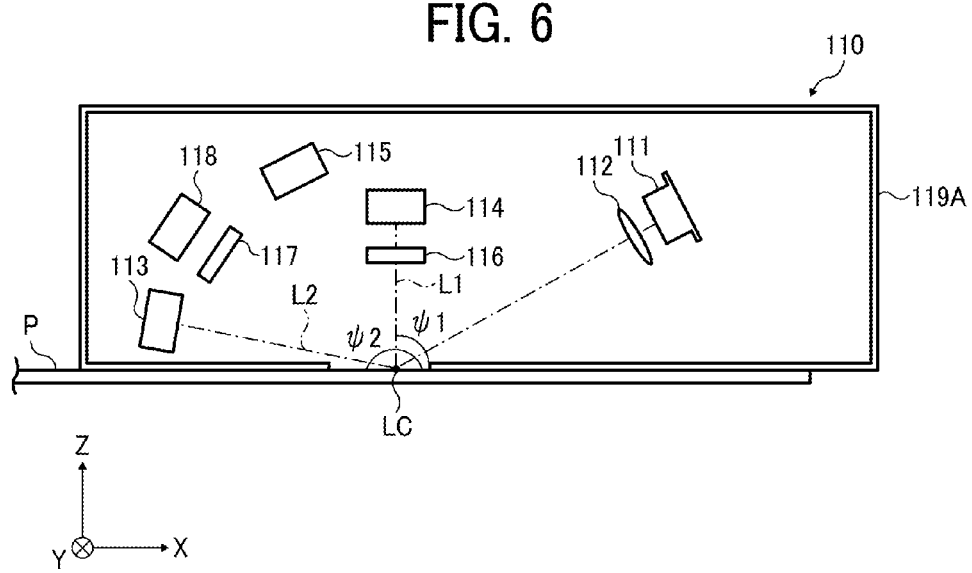
FIG. 6 is a diagram illustrating respective positions of receivers.

The receiver 114 is disposed on the +Z side of the polarizing filter 116 and functions as a light receiver to receive the light transmitted through the polarizing filter 116. As illustrated in FIG. 6, a line L1 connects the center of light emission, a center of the polarizing filter 116, and a center of the receiver 114. The line L1 and the surface of the sheet P form an angle ψ1 of 90 degrees.

The receiver 113 is disposed on the +X side of the center of light emission with respect to an X axis. As illustrated in FIG. 6, a line L2 connects the center of light emission and a center of the receiver 113. The line L2 and the surface of the sheet P form an angle ψ2 of 170 degrees.

A center of the light source 111, the center of light emission, the center of the polarizing filter 116, and respective centers of the receivers 113, 114, 115, and 118 fall on the substantially identical vertical plane.

The reflection light reflected on the sheet P when the sheet P is irradiated can be separated to reflection light reflected on the surface of the sheet P and reflection light reflected from an inside of the sheet P. Further, the reflection light reflected on the surface of the sheet P can be separated to specular reflection light (SRL) and diffused reflection light (DRL).

Figure 7A:
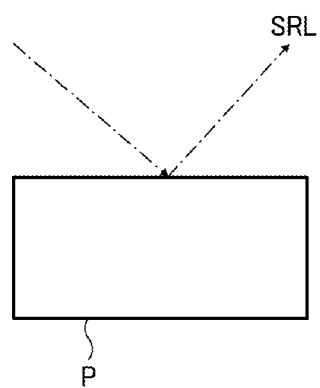
FIG. 7A is a diagram illustrating a surface specular reflection light.
Figure 7B:
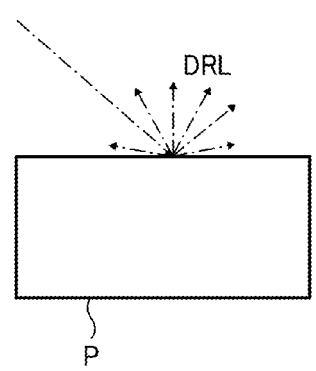
FIG. 7B is a diagram illustrating a surface diffused reflection light.
Figure 7C:
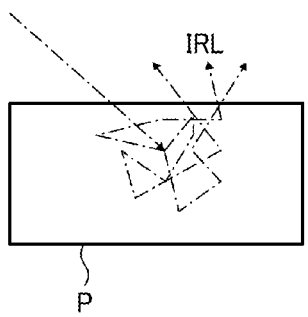
FIG. 7C is a diagram illustrating an internal reflection light.

For convenience, the specular reflection light reflected on the surface of the sheet P is hereinafter referred to as a "surface specular reflection light (SRL)" (see FIG. 7A) and the diffused reflection light reflected on the surface of the sheet P is hereinafter referred to as a "surface diffused reflection light (DRL)" (see FIG. 7B).

The surface of the sheet P includes plane portions and sloped portions. Based on a rate of the plane portions and the sloped portions, smoothness of the surface of the sheet P is determined. The light reflected on the plane portions becomes the surface specular reflection light and the light reflected on the sloped portions becomes the surface diffused reflection light. The surface diffused reflection light is the light fully reflected from an object (i.e., the sheet P) and a reflection direction has isotropy. As smoothness increases, the level of the surface specular reflection light rises.

By contrast, when the sheet P is a regular printing sheet, the reflection light reflected from the inside of the sheet P scatters in the fibers of the sheet P. Therefore, the reflection light is the diffused reflection light because the light scatters multiply in the sheet P. Hereinafter, for convenience, the reflection light reflected from the inside of the sheet P is also referred to as an "internal reflection light (IRL)" (see FIG. 7C). Similar to the surface diffused reflection light, the internal reflection light is the light fully reflected from an object (i.e., the sheet P) and the reflection direction is isotropic.

The polarization directions of the surface specular reflection light and the surface diffused reflection light toward the receiver (i.e., the receiver 114) are the same as the polarization direction of the incident light.

In order to rotate the polarization direction on the surface of the sheet S, the incident light is reflected on the sloped surface that is slanted to the rotation of the polarization direction with respect to an incident direction. Here, since the center of the light source (i.e., the light source 111), the center of light emission, and the center of each receiver (i.e., the receivers 113 and 114) fall on the same plane, the reflection light in the polarization direction rotated on the surface of the sheet P is not reflected in any direction of the receiver.

By contrast, the polarization direction of the internal reflection light is rotated with respect to the polarization direction of the incident light. It is thought that the light entered into the inside of the sheet (i.e., the sheet P) passes through the fibers of the sheet and optically rotates during multiple scattering in the sheet, thereby rotates the polarization direction.

Figure 8:
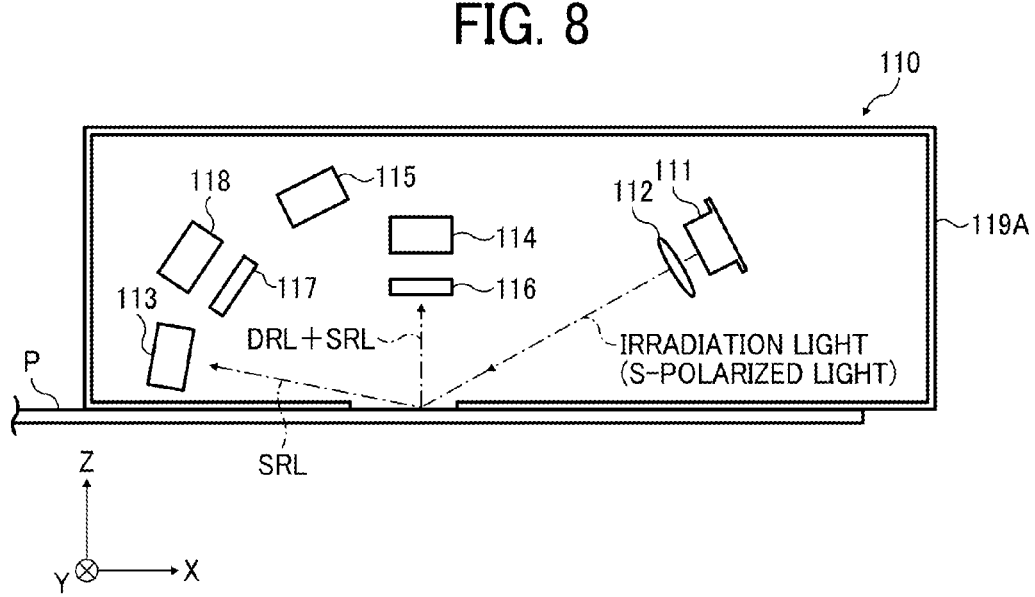
FIG. 8 is a diagram illustrating the light received by receivers.
Figure 9:
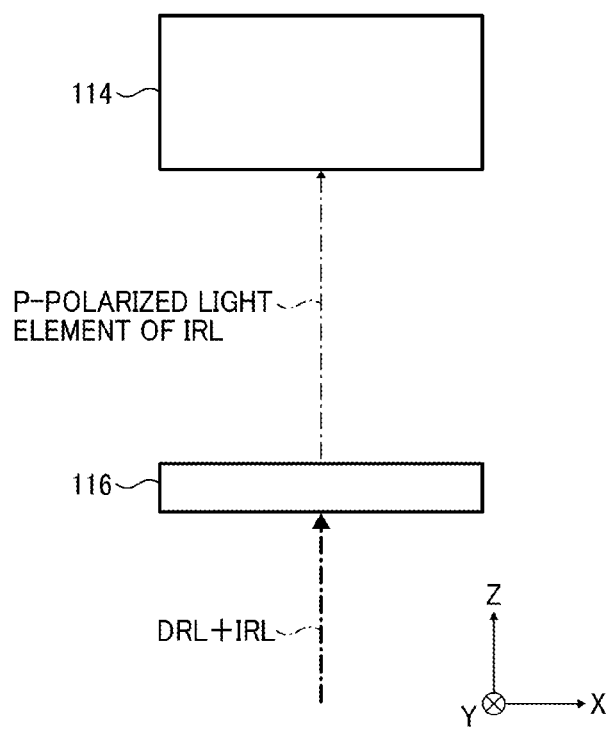
FIG. 9 is a diagram illustrating an incident light to a diffusion filter.

The reflection light including the surface diffused reflection light and the internal reflection light enters into the polarizing filter 116, as illustrated in FIG. 8.

Since the surface diffused reflection light is the S-polarized light that is the same as the incident light. Therefore, the polarizing filter 116 blocks or reflects the surface diffused reflection light. By contrast, the internal reflection light includes both the S-polarized light and the P-polarized light. Therefore, a component of the P-polarized light passes through the polarizing filter 116. Specifically, the component of the P-polarized light contained in the internal reflection light is received by the receiver 114 (see FIG. 9).

It is to be noted that the component of the P-polarized light included in the internal reflection light is also referred to as a "P-polarized light internal reflection light", for convenience. In addition, a component of the S-polarized light included in the internal reflection light is also referred to as an "S-polarized light internal reflection light".

The level of the P-polarized light internal reflection light is proved to have a correlation to thickness and density of the sheet P. It is because the level of the P-polarized light internal reflection light depends on a path length when the sheet P passes through the fibers in the sheet.

The receiver 113 receives reflection light having the surface specular reflection light, the surface diffused reflection light, and the internal reflection light. At this light receiving position, the level of the surface diffused reflection light and the level of the internal reflection light are significantly smaller than the level of the surface specular reflection light. Therefore, it is regarded as that the level of light received by the receiver 113 substantially corresponds to the level of the surface specular reflection light (see FIG. 8).

Figure 10:
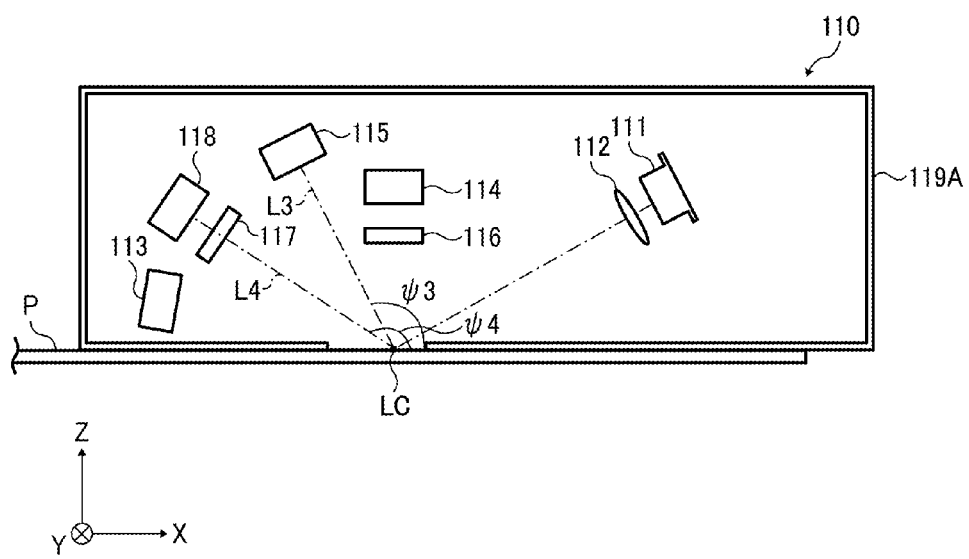
FIG. 10 is a diagram illustrating respective positions of different receivers.

The receiver 115 that functions as a light receiver is disposed at a position to receive the surface diffused reflection light and the internal reflection light. For example, as illustrated in FIG. 10, a line L3 connects the center of light emission and a center of the receiver 115. The line L3 and the surface of the sheet P form an angle $\psi3$ of 120 degrees. The center of the light source 111, the center of light emission, the center of the polarizing filter 116, and the respective centers of the receivers 113, 114, 115, and 118 fall on the substantially same vertical plane.

The polarizing filter 117 is disposed on the light path of the surface diffused reflection light and the internal reflection light. The polarizing filter 117 is a polarizing filter that transmits the P-polarized light and blocks or reflects the S-polarized light.

The receiver 118 is disposed on a light path of the light transmitted through the polarizing filter 117. The receiver 118 receives a component of the P-polarized light included in the internal reflection light.

For example, as illustrated in FIG. 10, a line L4 connects the center of light emission, a center of the polarizing filter 117, and a center of the receiver 118. The line L4 and the surface of the sheet P form an angle $\psi4$ of 150 degrees. The center of the light source 111, the center of light emission, the center of the polarizing filter 116, the center of the polarizing filter 117, and the respective centers of the receivers 113, 114, 115, and 118 fall on the substantially same vertical plane.

The receiver 160 illustrated in FIG. 3 functions as a transmitted light receiver and is disposed at a position to receive a light beam that is transmitted through the sheet P out of the light beams emitted from the light source 111 and irradiated to the sheet P.

The receivers 113, 114, 115, 118, and 160 output respective electrical signals (current signals) corresponding to respective received light levels to the light emission processing unit 130.

As illustrated in FIG. 3, the light emission processing unit 130 includes a light source driver 131, a current-to-voltage converter 132, and an analog-to-digital (AD) converter 133. The light emission processing unit 130 is connected to the dark box 119A.

The light source driver 131 outputs the light source driving signal to the light source 111 according to instructions issued by the controller 600.

The current-to-voltage converter 132 converts current signals inputted by each receiver to voltage signals.

The AD converter 133 converts analog signals passing through the current-to-voltage converter 132 to digital signals and outputs the converted digital signals to the controller 600.

As described in this example, by including information obtained by the receiver 160 that receives a transmitted light in addition to information obtained by the receivers 113, 114, 115, and 118 receiving the reflection light, the sheet discriminator 100 can discriminate the type of the sheet P more precisely.

A thickness of the sheet P can be obtained as information of the sheet P based on the levels of transmitted light received by the receiver 160. When the sheet P is not inserted into the sheet discriminator 100 through the opening 102 and is not located between the light source 111 and the receiver 160, the receiver 160 receives a constant amount of light emitted from the light source 111.

When the sheet P is inserted into the opening 102 and located between the light source 111 and the receiver 160, the level of light received by the receiver 160 varies according to the thickness of the sheet P. Based on the light level, the controller 600 can obtain the thickness of the sheet P with transform expressions and conversion tables, both of which are previously prepared to convert the light level to an amount of thickness of the sheet P.

By contrast, as described above, the sheet discriminator 100 according to this example includes the sheet thickness detecting sensor 170 to detect the thickness of the sheet P that is inserted into the opening 102 is provided, separately from the sheet information detecting sensor 110.

Figure 11:
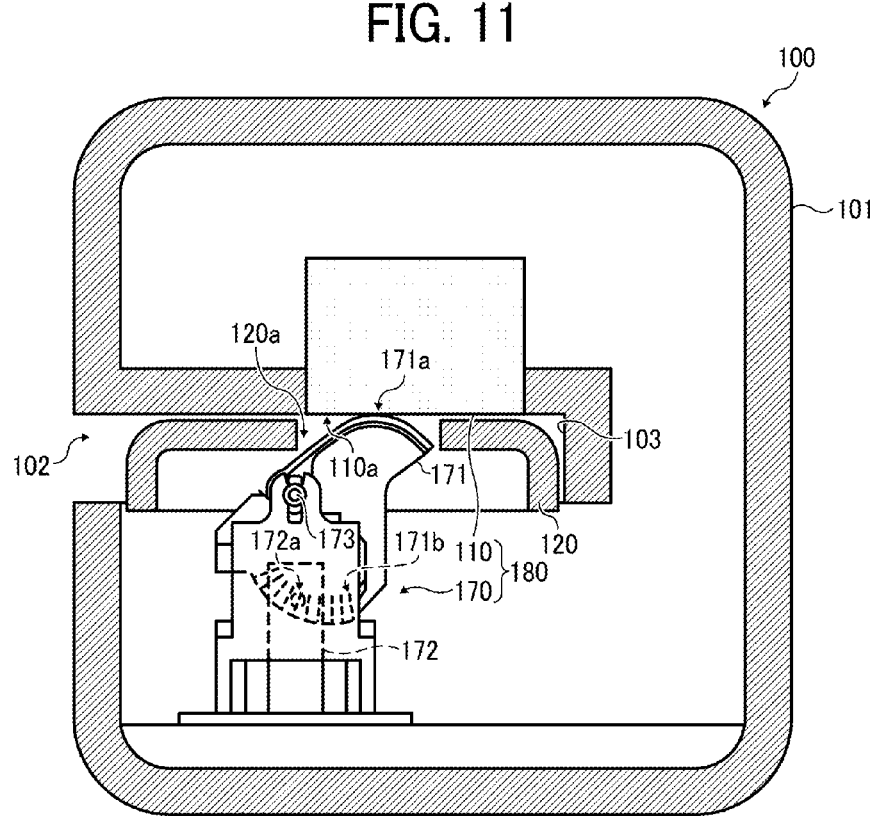
FIG. 11 is a cross sectional view illustrating a configuration of a sheet discriminator, sectioned along a line corresponding to a length of a slit formed on a sheet loading table.

FIG. 11 is a cross sectional view illustrating a configuration of the sheet discriminator 100, sectioned along a line corresponding to a length of a slit 120a formed on the sheet loading table 120.

It is to be noted that the biasing members 150 to bias the sheet loading table 120 as illustrated in FIGS. 2A and 2B are omitted in FIG. 11.

The sheet thickness detecting sensor 170 is an encoder that functions as a displacement detector to detect an amount of displacement according to the thickness of the sheet P. As illustrated in FIG. 11, the sheet thickness detecting sensor 170 includes a feeler 171 and a transmission type optical sensor 172.

The feeler 171 that functions as a displacement gauge has multiple slits 171b formed at constant angled pitches.

The transmission type optical sensor 172 that functions as a displacement detector detects the multiple slits 171b of the feeler 171.

Figure 12:
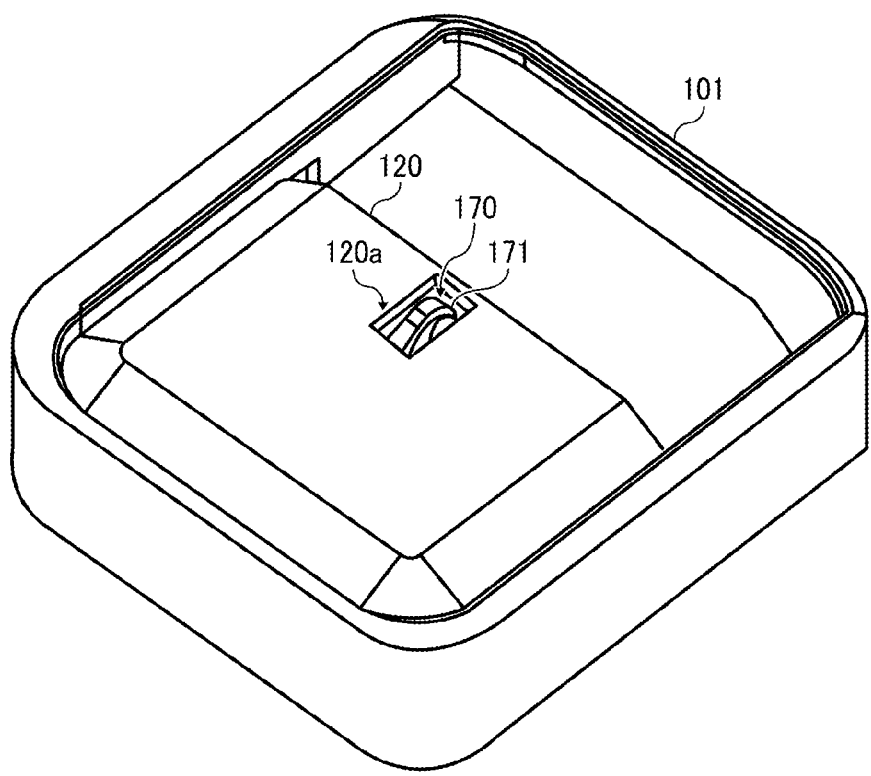
FIG. 12 is a perspective view illustrating a lower part of the sheet discriminator with an upper part of a feeler exposed from the slit formed on the sheet loading table.

FIG. 12 is a perspective view illustrating a lower part of the sheet discriminator 100.

As illustrated in FIG. 12, an upper part of the feeler 171 of the sheet thickness detecting sensor 170 is exposed from the slit 120a formed on the sheet loading table 120 so that the upper part of the feeler 171 is located on a path of insertion of the sheet P in the gap formed between the sheet loading table 120 and the sheet information detecting sensor 110.

When the sheet P is not inserted in the opening 102, the feeler 171 is located at an initial position at which an upper end 171a of the feeler 171 is in contact with a bottom face 110a of the sheet information detecting sensor 110, which functions as an opposing member. When the feeler 171 is at the initial position, the sheet P is not sandwiched by the feeler 171 and the sheet information detecting sensor 110, and therefore the sheet thickness detecting sensor 170 detects the thickness of the sheet P as "0".

Figure 13A:
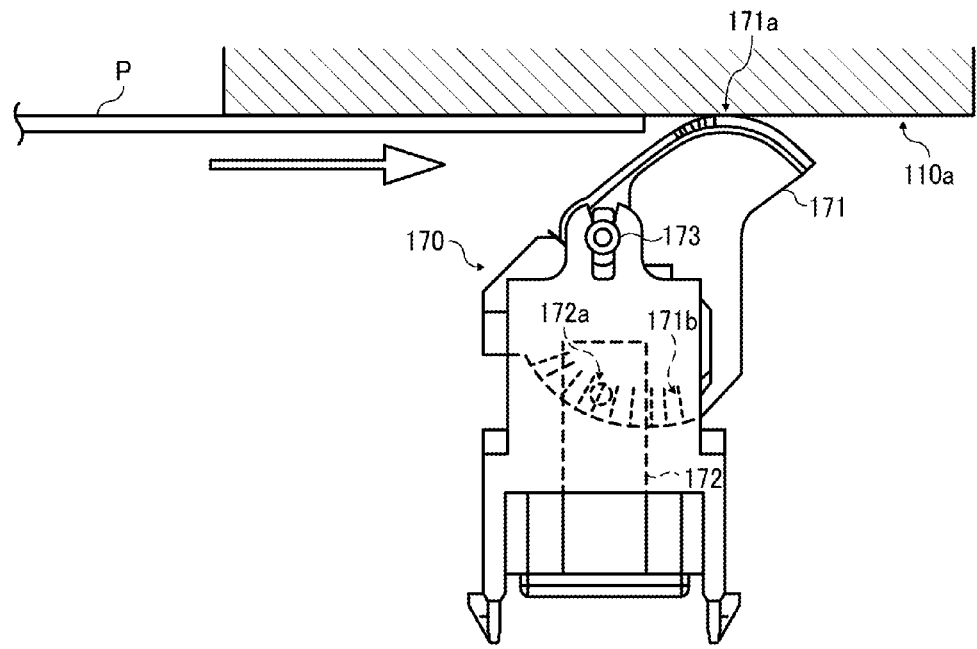
FIG. 13A is a diagram illustrating a state immediately before a sheet passes a contact position of an upper end of the feeler and a bottom face of a sheet information detecting sensor.
Figure 13B:
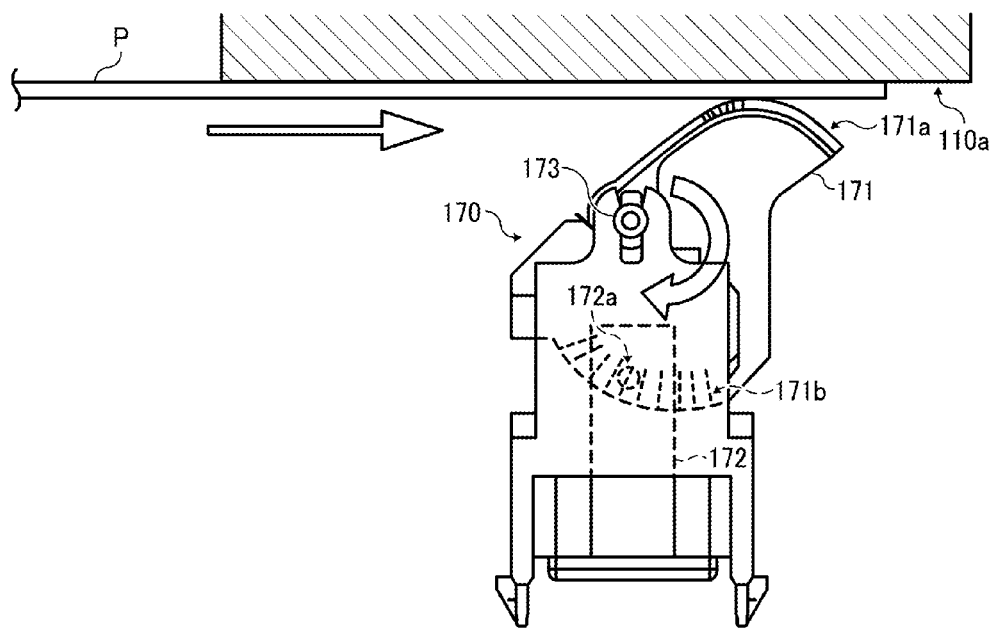
FIG. 13B is a diagram illustrating a state in which the sheet is passing the contact part of FIG. 13A.

FIG. 13A is a diagram illustrating a state immediately before the sheet P passes a contact position of the upper end 171a of the feeler 171 and the bottom face 110a of the sheet information detecting sensor 110. FIG. 13B is a diagram illustrating a state in which the sheet P is passing the contact part of FIG. 13A.

As illustrated in FIG. 13A, when the sheet P is inserted into the opening 102 to pass the contact position where the upper end 171a of the feeler 171 and the bottom face 110a of the sheet information detecting sensor 110, the sheet P presses the feeler 171. Consequently, as illustrated in FIG. 13B, the feeler 171 rotates about a rotary shaft 173 thereof in a clockwise direction in FIG. 13B. Accordingly, the sheet P is sandwiched between the feeler 171 and the sheet information detecting sensor 110.

At this time, the optical sensor 172 detects the multiple slits 171b passing a position facing a sensor part 172a thereof, and a rotation amount of the feeler 171 is obtained based on detection results of the optical sensor 172. The thus obtained rotation amount of the feeler 171 is then converted to an amount of thickness of the sheet P by a given expression or equation. Accordingly, the thickness of the sheet P can be obtained.

It is to be noted that the configuration of the sheet thickness detecting sensor 170 is not limited to the above-described configuration. For example, any configuration including a displacement sensor that can detect the thickness of the sheet P can be applied to this disclosure.

The thickness of the sheet P can be obtained using the sheet information detecting sensor 110. Specifically, the light emitted by the light source 111 and transmitted through the sheet P is received by the receiver 160. Based on the results obtained by this operation, the thickness of the sheet P can be detected. However, as the sheet P becomes thicker, the receiver 160 receives a lower level of transmitted light.

For this reason, depending on the sensitivity of the receiver 160, it is likely that the level of the transmitted light received by the receiver 160 is too low to detect the thickness of the sheet P properly. Therefore, when a thick paper is employed as the sheet P, the thickness of the sheet P cannot be detected accurately and, as a result, accuracy of sheet discrimination is likely to be degraded.

By contrast, by employing the sheet thickness detecting sensor 170 to detect the thickness of the sheet P as described above, the thickness of the sheet P can be detected more accurately compared to the case in which the thickness of the sheet P is obtained based on detection results of the transmitted light received by the receiver 160.

Specifically, the sheet thickness detecting sensor 170 detects the thickness of the sheet P based on an amount of displacement of the feeler 171 whose position is physically changed from the initial position according to the thickness of the sheet P. Accordingly, even though the sheet P has a thickness difficult for the sheet information detecting sensor 110 to precisely detect optically, the sheet thickness detecting sensor 170 that functions as a sheet thickness detector can detect the thickness of the sheet P accurately.

Therefore, by including the detection results obtained by the sheet thickness detecting sensor 170 to sheet information used to distinguish the sheet P by the controller 600, the sheet P can be discriminate using information regarding the sheet P having the thickness detected precisely. As a result, the sheet discriminator 100 can prevent degradation of accuracy of sheet discrimination due to inaccurate detection of the thickness of the sheet P when a thick paper is used as the sheet P.

It is to be noted that, when the sheet P is a thin paper, the level of transmitted light through the sheet P is high. Therefore, the thickness of the sheet P can be detected relatively precisely based on the level of transmitted light received by the receiver 160.

Therefore, for example, when the thickness of the sheet P detected by the sheet thickness detecting sensor 170 is lower (thinner) than a given thickness previously set, the level of light received by the receiver 160 is additionally used as sheet information to obtain the thickness of the sheet P. By so doing, the sheet thickness detecting sensor 170 can detect the thickness of the sheet P more accurately when the sheet P is a thin paper, and accuracy in sheet discrimination can be more enhanced.

Figure 14:
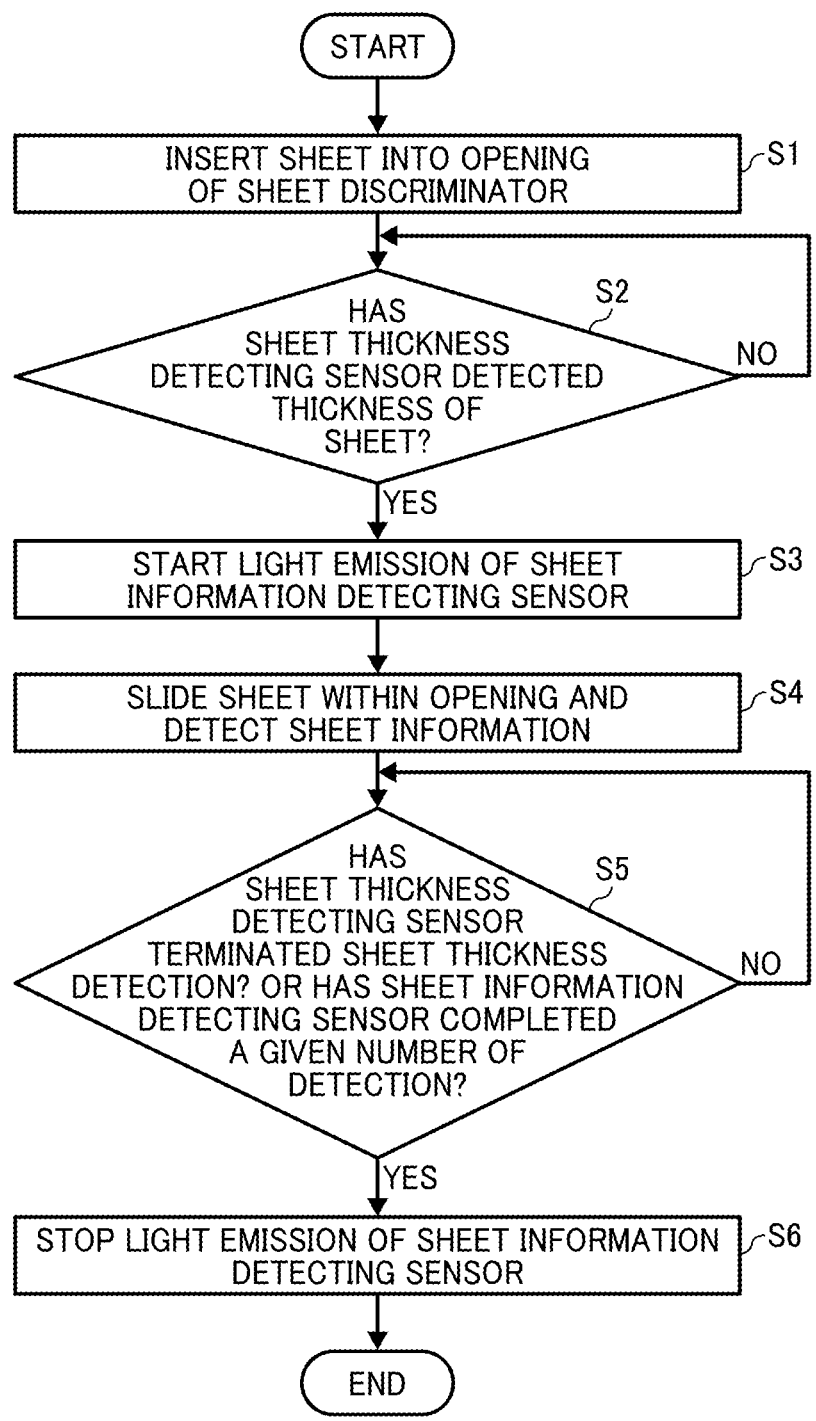
FIG. 14 is a flowchart illustrating an example of control of sheet discrimination performed by the sheet discriminator of FIG. 1.

Next, a description is given of control of sheet discrimination performed by the sheet discriminator 100 with reference to FIGS. 2A, 2B, and 14.

FIG. 14 is a flowchart illustrating an example of control of sheet discrimination performed by the sheet discriminator 100 according to this example.

As illustrated in FIG. 2A, the sheet P is inserted toward the end face 103 of the opening 102 of the sheet discriminator 100 in a direction indicated by arrow C, as described in step S1 in FIG. 14. When the sheet thickness detecting sensor 170 detects the thickness of the sheet P, which is YES in step S2 in FIG. 14, the sheet information detecting sensor 110 starts light emission, as described in step S3 in FIG. 14. When the sheet thickness detecting sensor 170 does not detect the thickness of the sheet P, which is NO in step S2 in FIG. 14, the procedure is repeated until the sheet thickness detecting sensor 170 detects thickness of the sheet P.

The sheet information detecting sensor 110 performs at least one information detection D1 in FIG. 2A with respect to the sheet P that is further inserted toward the end face 103. After the sheet P has reached the end face 103 of the opening 102, the sheet P is removed. When pulling out the sheet P from the opening 102, the sheet P moves in a direction indicated by arrow D in FIG. 2B. Hereinafter, the at least one information detection D1 is occasionally referred to as a first information detection(s) D1.

At this time, the sheet information detecting sensor 110 performs at least another one information detection D2 in FIG. 2B. Hereinafter, the at least another one information detection D2 is occasionally referred to as a second information detection(s) D2. Accordingly, the sheet information detecting sensor 110 detects the sheet P at different points on the sheet P in the first information detection(s) D1 and the second information detection(s) D2.

As described above, the sheet discriminator 100 according to this example slides the sheet P in the opening 102 for multiple detections. Based on the information obtained by the sheet information detecting sensor 110, the controller 600 discriminates the sheet P, as described in step S4 in FIG. 14.

After the sheet P is removed from the opening 102 and is no longer detected by the sheet thickness detecting sensor 170, which is YES in step S5 in FIG. 14, the controller 600 causes the sheet information detecting sensor 110 to stop light emission, as described in step S6 in FIG. 14. Alternatively, after the sheet information detecting sensor 110 completes a given number of information detections, which is YES in step S5 in FIG. 14, the controller 600 causes the sheet information detecting sensor 110 to stop light emission, as described in step S6 in FIG. 14. When the sheet P is detected by the sheet thickness detecting sensor 170 and the sheet information detecting sensor 110 does not complete the given number of information detections, which is NO in step S5 in FIG. 14, the procedure is repeated until the condition of step S5 is satisfied.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise sheet discrimination of the sheet P can be performed.

Further, the sheet discriminator 100 according to this example causes the sheet information detecting sensor 110 to emit light when the sheet thickness detecting sensor 170 detects the thickness of the sheet P. By so doing, when the sheet P is inserted into the opening 102 of the sheet discriminator 100, the sheet information detecting sensor 110 can start light emission without any operator handling.

Further, when the sheet thickness detecting sensor 170 detects no thickness of the sheet P, the controller 600 causes the sheet information detecting sensor 110 to stop emitting light. By so doing, when the sheet P is pulled out from the opening 102 of the sheet discriminator 100, the sheet information detecting sensor 110 can stop light emission without any operator handling.

Further, in the sheet discriminator 100 according to this example, the sheet thickness detecting sensor 170 is used not only for detecting the thickness of the sheet P but also for detecting presence or absence of the sheet P at a given position on the sheet loading table 120.

Specifically, the sheet thickness detecting sensor 170 detects the thickness of the sheet P and, at the same time, detects the presence of the sheet P on the sheet loading table 120.

On the contrary, when the sheet thickness detecting sensor 170 detects no thickness of the sheet P (i.e., when the feeler 171 is located at the initial position and the thickness of the sheet is indicated as "0"), the sheet thickness detecting sensor 170 detects that there is no sheet on the sheet loading table 120.

Depending on whether or not the sheet thickness detecting sensor 170 detects the thickness of the sheet P, the controller 600 regulates timing to cause the light source 111 of the sheet information detecting sensor 110 to start or stop light emission.

By so doing, the light emission by the light source 111 is performed based on the timing. With this operation, the sheet information detecting sensor 110 performs light emission when the sheet information detecting sensor 110 detect information of the sheet P. Accordingly, when compared with a case in which the sheet information detecting sensor 110 constantly emits light, the sheet discriminator 100 according to this example can extend the life span of the sheet information detecting sensor 110 and reduce waste energy consumption thereof.

A sheet detecting sensor can be provided to the sheet discriminator 100 to detect whether the sheet P is present or absent at the given position so as to regulate the timing to cause the light source 111 to start or stop light emission based on the detection results obtained by the sheet detecting sensor. However, compared with the configuration including the sheet detecting sensor, the sheet discriminator 100 having the configuration without the sheet detecting sensor can reduce the cost related to the sheet detecting sensor.

Further, as illustrated in FIGS. 2A and 2B, the biasing members 150 press the sheet loading table 120 toward the sheet information detecting sensor 110. By so doing, a detection face of the sheet information detecting sensor 110 can contact or approach the sheet P. As a result, while reducing or preventing disturbances such as deformation of the sheet P and entry of ambient light, the sheet discriminator 100 can discriminate the type of the sheet P more precisely.

Further, in FIGS. 2A and 2B, the sheet information detecting sensor 110 is disposed on the upper side of the sheet discriminator 100 and the sheet loading table 120 is disposed on the lower side with the sheet discriminator 100 arranged therebetween. Specifically, the sheet loading table 120 is disposed below the sheet information detecting sensor 110. However, the positional relation of the sheet information detecting sensor 110 and the sheet loading table 120 is not limited thereto as long as a distance between the detection face of the sheet information detecting sensor 110 and the sheet P is secured and the detection face of the sheet information detecting sensor 110 can contact the sheet P.

However, the configuration in which the sheet information detecting sensor 110 is disposed above the sheet loading table 120 can avoid foreign materials brought into the sheet discriminator 100 via the sheet P and dust of the sheet P adhering and entering to the sheet information detecting sensor 110. Therefore, it is preferable that the sheet information detecting sensor 110 and the sheet loading table 120 have the positional relation as illustrated in FIGS. 2A and 2B.

Further, this configuration does not have any restriction in handling sheet discrimination. For example, no pressure is applied between the sheet information detecting sensor 110 and the sheet P, the sheet P is not deformed during a detecting operation, and a user does not have to apply any force when handling the sheet P. Therefore, data of the surface of the sheet P can be obtained easily.

It is to be noted that, at least, the sheet information detecting sensor 110 has a function to obtain information on the surface of the sheet P.

A light-emitting diode (LED) is generally employed as the light source 111 of the sheet information detecting sensor 110. By employing a surface emitting laser having VCSEL elements, surface information of the sheet P can be detected more precisely. Therefore, more precise detection results can be obtained.

Further, the sheet information detecting sensor 110 is preferably include at least a specular reflection light receiver (e.g., the receivers 113, 114, 115, and 118) to receive specular reflection light reflected on the sheet P and a diffused reflection light receiver (e.g., the receiver 113) to receive diffused reflection light reflected on the sheet P out of the light beams emitted from the light source 111 and irradiated to the sheet P. The sheet information detecting sensor 110 can be a known optical sensor.

Since the sheet information detecting sensor 110 has multiple sensors disposed at different angles to detect scattered light beams of diffused reflection light, more precise detection results of information can be obtained than the information obtained from specular reflection light alone.

Figure 15A:
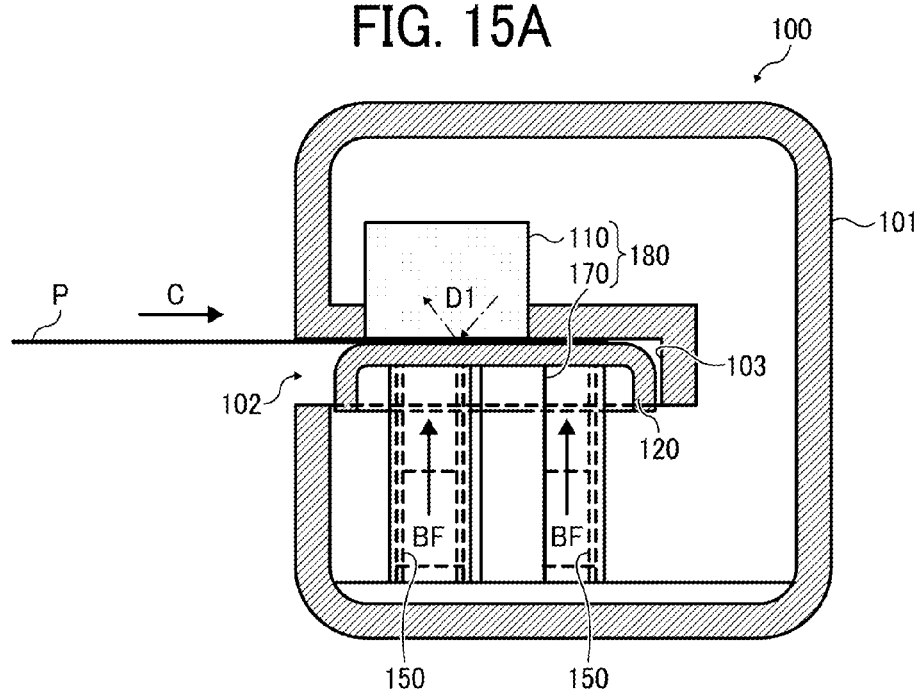
FIG. 15A is a cross sectional view illustrating the sheet discriminator when the sheet is inserted thereto through the opening.
Figure 15B:
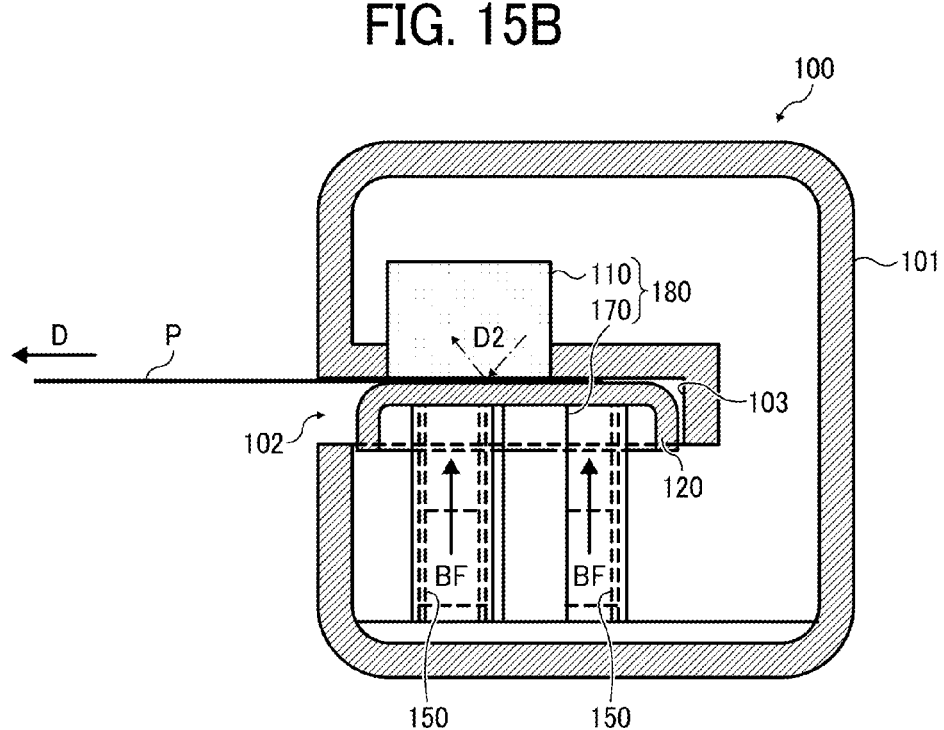
FIG. 15B is a cross sectional view illustrating the sheet discriminator when the sheet is pulled out from the opening of the sheet discriminator.

Now, a description is given of a sheet discriminator 100 according to another example of this disclosure, with reference to FIGS. 15A and 15B.

FIGS. 15A and 15B are cross sectional views of the sheet discriminator 100, viewed from a direction indicated by arrow A in FIG. 1. Specifically, FIG. 15A is a cross sectional view illustrating the sheet discriminator 100 when the sheet P is inserted thereto through the opening 102 of the sheet discriminator 100 and FIG. 15B is a cross sectional view illustrating the sheet discriminator 100 when the sheet P is pulled out from the opening 102 of the sheet discriminator 100.

In the sheet discriminator 100 according to this example, the sheet thickness detecting sensor 170 is located downstream from the sheet information detecting sensor 110 in a sheet inserting direction indicated by arrow C illustrated in FIGS. 15A and 15B. Specifically, the positions of the sheet information detecting sensor 110 and the sheet thickness detecting sensor 170 in the sheet inserting direction are switched from those illustrated in FIGS. 2A and 2B, and therefore the sheet thickness detecting sensor 170 is disposed closer to the end face 103 than the sheet information detecting sensor 110 is.

It is to be noted that the configuration and the controller of light emission of the light source 111 of the sheet information detecting sensor 110 of the sheet discriminator 100 illustrated in FIGS. 15A and 15B are basically identical to the configuration and the control of the sheet discriminator 100 illustrated in FIGS. 2A and 2B, except for the above-described positional relation of the sheet information detecting sensor 110 and the sheet thickness detecting sensor 170. Therefore, detailed descriptions of the other components and functions are omitted here.

By disposing the sheet thickness detecting sensor 170 downstream from the sheet information detecting sensor 110 in the sheet inserting direction to the opening 102, this sheet discriminator 100 can achieve the following effects.

In the configuration of the sheet discriminator 100 according to this example, as illustrated in FIGS. 15A, and 15B, when the sheet P is detected by the sheet thickness detecting sensor 170, the sheet P has reached a position facing a sheet information detectable position of the sheet information detecting sensor 110. Therefore, when the sheet P is inserted into the opening 102, the controller 600 causes the sheet information detecting sensor 110 to start light emission in a state in which the sheet P has reached the position facing the sheet information detecting sensor 110.

Accordingly, the above-described configuration of the sheet discriminator 100 illustrated in FIGS. 15A and 15B can reduce a time period from the start of light emission of the sheet information detecting sensor 110 to the detection when compared with the configuration of the sheet discriminator 100 in which the sheet information detecting sensor 110 starts light emission and the sheet P reaches at the position facing the sheet information detecting sensor 110. Since the time of light emission of the sheet information detecting sensor 110 can be reduced, the sheet discriminator 100 according to this example can extend the life span of the sheet information detecting sensor 110 and reduce waste energy consumption thereof.

Next, a description is given of a configuration of an image forming system 1 according to another example of this disclosure, with reference to FIG. 16.

As illustrated in FIG. 16, the image forming system 1 includes an image forming apparatus 2 and a sheet finishing apparatus 3 that functions as a sheet finisher.

Further, the sheet discriminator 100 is disposed in the image forming system 1 outside the image forming apparatus 2. Details of the sheet discriminator 100 is described below.

The image forming apparatus 2 and the sheet finishing apparatus 3 are connected to communicate with each other. In the image forming system 1, after the image forming apparatus 2 has formed an image on the sheet P, the sheet finishing apparatus 3 accepts the sheet P from the image forming apparatus 2 for various post-processing operations to the sheet P.

The post-processing operations include, for example, a corner binding process, a center folding process, and the like. The center folding process includes a center binding process. The sheet finishing apparatus 3 that executes the above-described various post-processing operations includes a sheet discharge mode, a corner binding mode, and a center binding mode.

Figure 17:
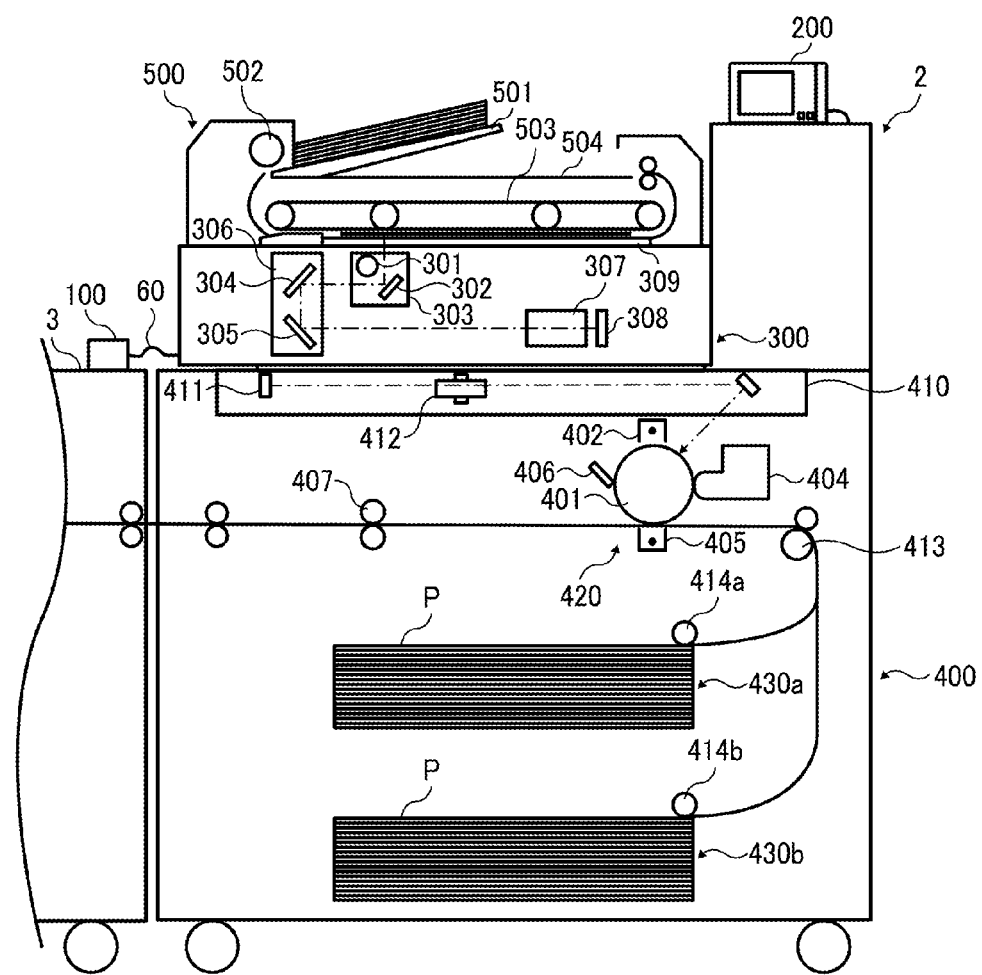
FIG. 17 is a diagram illustrating a configuration of an image forming apparatus included in the image forming system of FIG. 16.

FIG. 17 is a diagram illustrating a configuration of the image forming apparatus 2 included in the image forming system 1 of FIG. 16.

The image forming apparatus 2 may be a copier, a printer, a scanner, a facsimile machine, a plotter, and a multifunction peripheral or a multifunction printer (MFP) having at least one of copying, printing, scanning, facsimile, and plotter functions, or the like. According to the present example, the image forming apparatus 2 is an electrophotographic printer that forms toner images on a sheet or sheets by electrophotography.

More specifically, the image forming apparatus 2 functions as a printer. However, the image forming apparatus 2 can expand its function as a copier by adding a scanner as an option disposed on top of an apparatus body of the image forming apparatus 2. The image forming apparatus 2 can further obtain functions as a facsimile machine by adding an optional facsimile substrate in the apparatus body of the image forming apparatus 2.

Further, this disclosure is also applicable to image forming apparatuses adapted to form images through other schemes, such as known ink jet schemes, known toner projection schemes, or the like as well as to image forming apparatuses adapted to form images through electro-photographic schemes.

The image forming apparatus 2 includes an apparatus body 400, an image reading device 300, and an automatic document feeder (ADF) 500.

The apparatus body 400 encases an image forming part 420 and sheet trays 430a and 430b therein. The sheet trays 430a and 430b are vertically disposed below the image forming part 420. The sheet trays 430a and 430b have sheet feed rollers 414a and 414b, respectively, and accommodate the sheet P that functions as a recording medium. After the sheet P being fed by a selected one of the sheet feed rollers 414a and 414b, the sheet P accommodated in each of the sheet trays 430a and 430b is conveyed upwardly along a corresponding sheet conveying path before reaching a registration roller pair 413.

The image forming part 420 includes a photoconductor drum 401 that functions as an image bearer, a charger 402, an exposing device 410, a developing device 404, a transfer device 405, and a cleaning device 406.

The charger 402 uniformly charges a surface of the photoconductor drum 401.

The exposing device 410 is a latent image forming device to form an electrostatic latent image on the surface of the photoconductor drum 401 based on image data read by the image reading device 300.

The developing device 404 supplies toner to adhere to the electrostatic latent image formed on the surface of the photoconductor drum 401 and develops the electrostatic latent image into a visible toner image.

The transfer device 405 is an image transfer body to transfer the visible toner image on the photoconductor drum 401 onto the sheet P.

The cleaning device 406 is a cleaner to remove residual toner remaining on the surface of the photoconductor drum 401 after transfer of the toner image onto the sheet P.

The image forming apparatus 2 further includes a fixing device 407 that is disposed downstream from the image forming part 420 in a sheet conveying direction. The fixing device 407 functions as a fuser to fix the toner image to the sheet P.

The exposing device 410 include a laser unit 411 and a polygon mirror 412.

The laser unit 411 emits laser light based on the image data under control of a controller provided to the apparatus body 400.

The polygon mirror 412 scans the laser light emitted by the laser unit 411 in a direction of rotation axis of the photoconductor drum 401 (i.e., in a main scanning direction).

The image reading device 300 functions as an image reader to read image data of an original document.

The ADF 500 is disposed above the image reading device 300 and is connected to the image reading device 300. The ADF 500 includes a document table 501, a document feed roller 502, a transfer belt 503, and a document discharging tray 504.

When original documents are set on the document table 501, upon receipt of a signal to start reading image data of the original documents, the document feed roller 502 of the ADF 500 feeds the original documents placed on the document table 501 one by one. Each original document fed by the document feed roller 502 is guided by the transfer belt 503 to a contact glass 309 and is halted on the contact glass 309 temporarily.

With the original document halted on the contact glass 309, the image reading device 300 reads the image data of the original document. Thereafter, the transfer belt 503 resumes to convey the original document to the document discharging tray 504.

Next, a description is given of a series of image reading processes and a series of image forming processes.

Either when the ADF 500 feeds the original document to the contact glass 309 or when a user places the original document on the contact glass 309 manually and inputs a copy start instruction via a control panel 200, a light source 301 mounted on a first moving unit 303 emits light. Along with the light emission, the first moving unit 303 and a second moving unit 306 are moved along a guide rail.

As the light source 301 emits the light onto the original document placed on the contact glass 309, the reflection light reflects on the original document. The reflection light is guided to a mirror 302 mounted on the first moving unit 303 and mirrors 304 and 305 mounted on the second moving unit 306 to a lens 307 so as to be received by a CCD 308. As a result, the CCD 308 reads the image data of the original document and the read image data is converted from analog data to digital data by an analog/digital (A/D) conversion circuit provided to the image forming apparatus 2. The image data is then transmitted from a data output port of the image reading device 300 to the controller of the apparatus body 400.

By contrast, the apparatus body 400 starts driving the photoconductor drum 401. As the photoconductor drum 401 rotates at a given speed, the charger 402 uniformly charges the surface of the photoconductor drum 401. The exposing device 410 then exposes light to the surface of the photoconductor drum 401 to form the electrostatic latent image based on the image data read by the image reading device 300.

Then, the developing device 404 develops the electrostatic latent image formed on the surface of the photoconductor drum 401 into a visible toner image. The sheet P is fed from a selected one of the sheet trays 430a and 430b by a corresponding one of the sheet feed rollers 414a and 414b and temporarily stopped at the registration roller pair 413.

In synchronization with timing at which the leading end of the toner image formed on the surface of the photoconductor drum 401 reaches an image transfer part that is located facing the transfer device 405, the registration roller pair 413 conveys the sheet P to the image transfer part. When the sheet P passes the image transfer part, the toner image formed on the surface of the photoconductor drum 401 is transferred onto the sheet P due to an action of an electric field in a transfer nip region.

Thereafter, the sheet P having the toner image on the surface thereof is conveyed to the fixing device 407 so that the fixing device 407 fixes the toner image to the sheet P. Then, the sheet P is discharged to the sheet finishing apparatus 3.

It is to be noted that residual toner remaining on the surface of the photoconductor drum 401 without being transferred onto the sheet P at the image transfer part is removed from the photoconductor drum 401 by the cleaning device 406.

Figure 18:
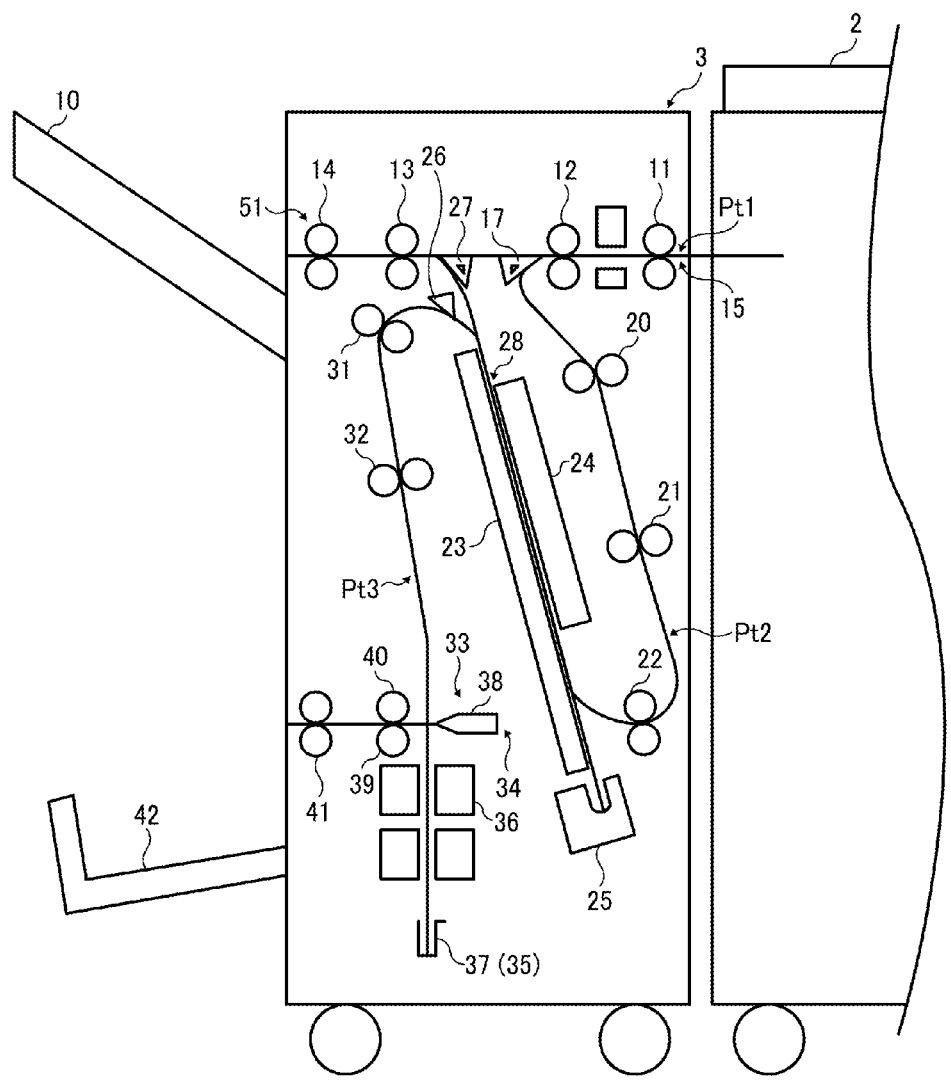
FIG. 18 is a diagram illustrating a configuration of a sheet finisher included in the image forming system of FIG. 16.

A description is given of the sheet finishing apparatus 3 with reference to FIG. 18.

FIG. 18 is a diagram illustrating a configuration of the sheet finishing apparatus 3 included in the image forming system 1 illustrated in FIG. 16.

The sheet finishing apparatus 3 includes a first conveying path Pt1, a second conveying path Pt2, and a third conveying path Pt3. The first conveying path Pt1 is a path through which the sheet P discharged from the image forming apparatus 2 travels to a first sheet discharging tray 10. The second conveying path Pt2 branches from the first conveying path Pt1 to perform a side-stitching operation to a bundle of sheets. The third conveying path Pt3 is connected to the second conveying path Pt2 to perform a saddle-stitched center-folded sheet bundling operation to the bundle of sheets.

The first conveying path Pt1, the second conveying path Pt2, and the third conveying path Pt3 are defined by guide members, for example.

The first conveying path Pt1 includes an entrance roller 11, a sheet conveying roller 12, a sheet conveying roller 13, and a sheet discharging roller 14, which are disposed in this order along the first conveying path Pt1 from an upstream side to a downstream side of the sheet conveying direction.

The entrance roller 11, the sheet conveying roller 12, the sheet conveying roller 13, and the sheet discharging roller 14 are driven by a motor that functions as a driving source to convey a sheet of paper (i.e., the sheet P).

The first conveying path Pt1 further includes an entrance sensor 15 disposed upstream from the entrance roller 11 in the sheet conveying direction. The entrance sensor 15 detects that the sheet P is conveyed into the sheet finishing apparatus 3.

A switching claw 17 is disposed downstream from the sheet conveying roller 12 in the sheet conveying direction. The switching claw 17 switches the position by pivoting to selectively guide the sheet P to one of a downstream side of the switching claw 17 in the first conveying path Pt1 in the sheet conveying direction and the second conveying path Pt2. The switching claw 17 is driven by a motor or a solenoid.

In a sheet discharging mode, the sheet P conveyed from the image forming apparatus 2 to the first conveying path Pt1 is conveyed by the entrance roller 11, the sheet conveying roller 12, the sheet conveying roller 13, and the sheet discharging roller 14 and is discharged to the first sheet discharging tray 10.

By contrast, in a side stitching mode and a saddle stitching mode, the sheet P entered into the first conveying path Pt1 is conveyed by the entrance roller 11 and the sheet conveying roller 12, has a course of direction changed by the switching claw 17, and is conveyed to the second conveying path Pt2.

The second conveying path Pt2 includes a sheet conveying roller 20, a sheet conveying roller 21, a sheet conveying roller 22, a sheet tray 23, a first sheet aligning part 24, and a side-stitching unit (a first stitching unit) 25.

The sheet conveying roller 20, the sheet conveying roller 21, and the conveying roller 22 are driven by a motor. The first sheet aligning part 24 is driven by the motor.

Switching claws 26 and 27 are disposed at a downstream side of the sheet tray 23 in the sheet conveying direction. The switching claws 26 and 27 pivot to switch respective positions, so that the sheet P is selectively guided to one of the downstream side of the switching claw 17 in the first conveying path Pt in the first conveying path Pt1 and the third conveying path Pt3. The switching claws 26 and 27 are driven by a motor or a solenoid, for example.

In the side stitching mode, multiple sheets P are sequentially loaded on the selected one of the sheet trays 23. By so doing, the bundle of sheets including the multiple sheets P loaded thereon is formed. At this time, the trailing end of the bundle of sheets contacts a first movable reference fence that is disposed on the sheet tray 23 to align a position of the bundle of sheets in the sheet conveying direction and a width position of the bundle of sheets by the first sheet aligning part 24.

The sheet tray 23, the first sheet aligning part 24, and the first movable reference fence form a first bundling part 28 that functions as a bundling part to make multiple sheets into a stacked sheet bundle. The first bundling part 28 further includes a motor to drive the first sheet aligning part 24 and a motor to drive the first movable reference fence.

The side-stitched sheet bundle is conveyed by the first movable reference fence to the first conveying path Pt1. Then, the sheet bundle is further conveyed by the sheet conveying roller 13 and the sheet discharging roller 14 to be discharged to the first sheet discharging tray 10.

Here, the sheet discharging roller 14 functions as a sheet discharging member to discharge the sheet bundle that is bundled by the side stitching unit 25. By contrast, in the center folding mode, the sheet P conveyed to the second conveying path Pt2 is conveyed to the third conveying path Pt3 by the sheet conveying rollers 20, 21, and 22, and the first movable reference fence.

The third conveying path Pt3 includes a sheet conveying roller 31, a sheet conveying roller 32, and a binding and folding part 33.

A motor drives the sheet conveying rollers 31 and 32 to convey the sheet P. The binding and folding part 33 includes a center folding part 34, a center stitching part (a second stitching unit) 35, and a second bundling part 36.

The sheet P conveyed to the third conveying path Pt3 is conveyed by the sheet conveying rollers 31 and 32 one by one to the second bundling part 36. As a result, a sheet bundle of layered multiple sheets P is made. Specifically, the second bundling part 36 makes a stacked sheet bundle with multiple sheets conveyed by a sheet conveying part 51 that includes the entrance roller 11 and the sheet conveying rollers 12, 20, 21, 22, 31, and 32.

At this time, the leading end of the sheet bundle including the sheets P contacts a second movable reference fence 37 to be aligned in the sheet conveying direction and contacts a second sheet aligning part to be aligned in a sheet width direction.

The center stitching part 35 stitches the sheet bundle at or in the vicinity of the center of the sheet bundle in the sheet conveying direction. The center-stitched sheet bundle is returned to a center folding position by the second movable reference fence 37. The second movable reference fence 37 is driven by a motor.

The center folding part 34 folds the sheet bundle at the center thereof in the sheet conveying direction. In the center folding part 34, a folding blade 38 is disposed to face the center of the sheet bundle at the center folding position in the sheet conveying direction. The folding blade 38 that is driven by a motor moves from right to left of FIG. 16 to fold the center of the sheet bundle in the sheet conveying direction to insert the sheet bundle between a lower pressure roller 39 and an upper pressure roller 40.

The folded sheet bundle is pressed by the lower pressure roller 39 and the upper pressure roller 40. The lower pressure roller 39 and the upper pressure roller 40 are driven by a motor.

The above-described center-folded sheet bundle is discharged by the lower pressure roller 39, the upper pressure roller 40, and a sheet discharging roller 41 to a second sheet discharging tray 42.

Figure 19:
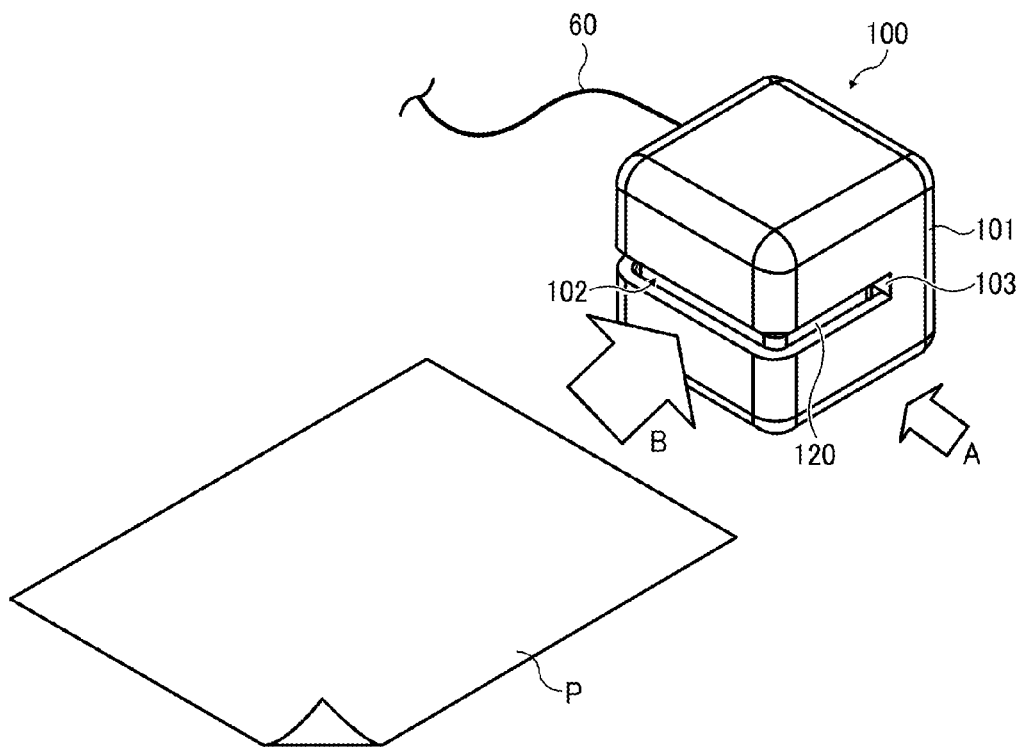
FIG. 19 is a diagram illustrating another configuration of a sheet discriminator included in the image forming system of FIG. 16.
Figure 20A:
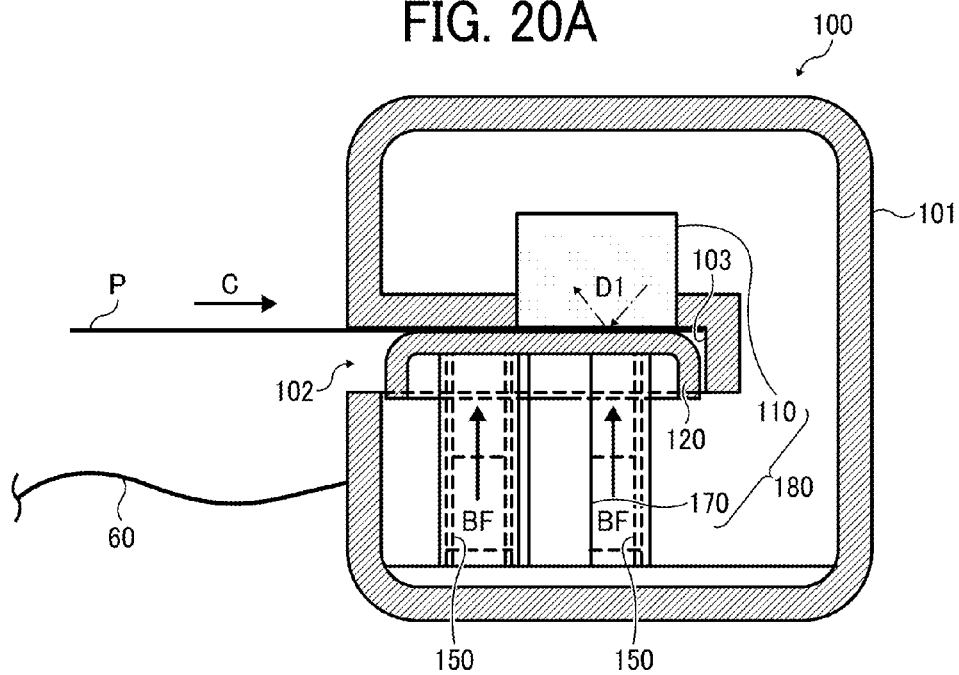
FIG. 20A is a cross sectional view illustrating the sheet discriminator when the sheet is inserted thereto through the opening.
Figure 20B:
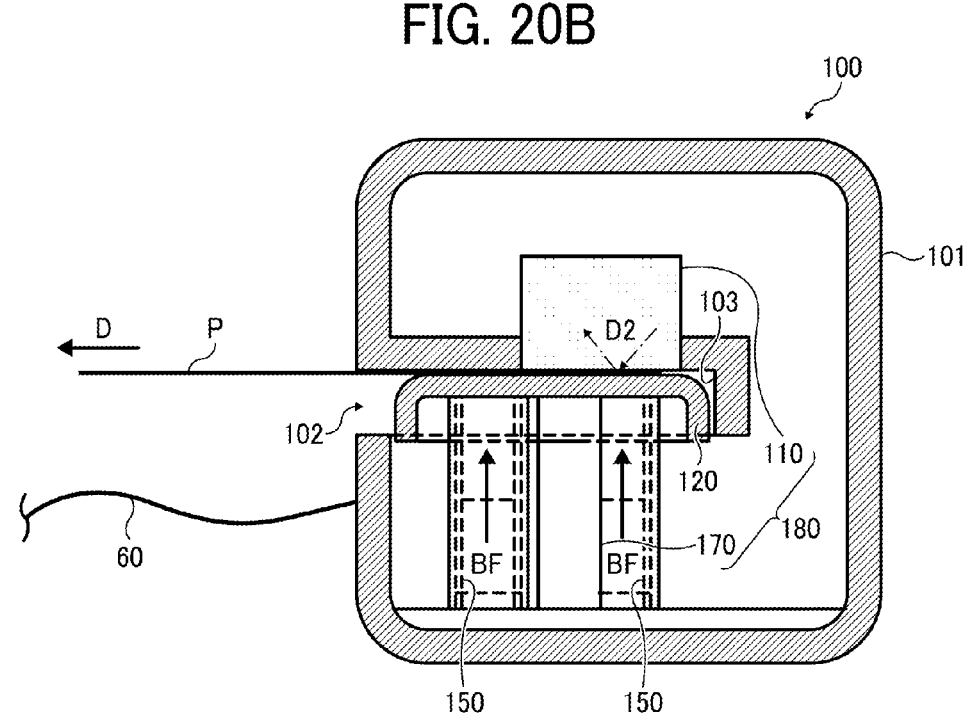
FIG. 20B is a cross sectional view illustrating the sheet discriminator when the sheet is pulled out from the opening of the sheet discriminator.
Figure 21:
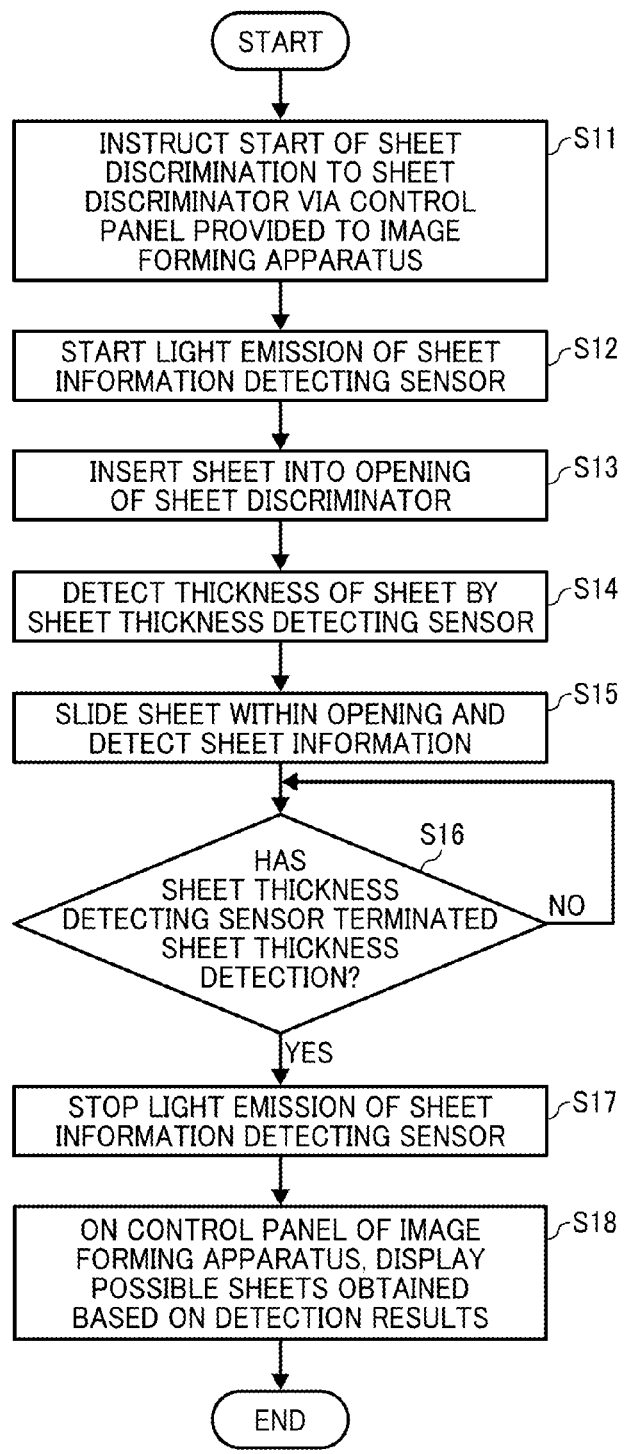
FIG. 21 is a flowchart illustrating an example of control of sheet discrimination performed by the sheet discriminator of FIG. 19.

A description is given of another example of the sheet discriminator 100 according to this example, with reference to FIGS. 19 through 21.

FIG. 19 is a diagram illustrating another configuration of the sheet discriminator 100 included in the image forming system 1 of FIG. 16.

Different from the previous example, this example includes the control panel 200 that functions as an indicator to indicate instructions to start sheet discrimination of the sheet P provided to the image forming apparatus 2. Specifically, in the previous example, when an image is sequentially formed on multiple sheets of the same type, for example, sheet discrimination of the sheet P starts on insertion of the sheet P into the opening 102 of the sheet discriminator 100 even if the sheet P can be used without sheet discrimination. By contrast, in this example, sheet discrimination of the sheet P is performed when the control panel 200 provided to the image forming apparatus 2 issues instructions to the sheet discriminator 100 to do so. The other parts and functions are basically identical to the configuration of the sheet discriminator 100 of the previous example.

As illustrated in FIG. 19, the sheet discriminator 100 according to this example is connected with the image forming apparatus 2 by a communication cable 60 that functions as a communicator. According to this configuration, the sheet discriminator 100 and the image forming apparatus 2 can communicate with each other.

The sheet P is inserted into the opening 102 of the sheet discriminator 100 that is connected to the image forming apparatus 2 via the communication cable 60 in the direction B until the sheet P contacts or approaches the end face 103 of the opening 102. By so doing, the sheet information related to sheet types determined by the sheet discriminator 100 according to this example is transmitted to the image forming apparatus 2 via the communication cable 60, so that appropriate image forming conditions can be set.

At this time, it is preferable that the operator grabs both left and right ends of the sheet P with respect to the direction B and inserts the sheet while checking that the sheet P has no deformation such as wrinkle or crease on the sheet P. It is to be noted that sheet insertion to the opening 102 is not limited to the above-described way but is applicable with any way of sheet insertion as long as the sheet P can be inserted into the opening 102 of the sheet discriminator 100 horizontally.

A description is given of a control of sheet discrimination with reference to FIGS. 20A, 20B, and 21.

FIGS. 20A and 20B are cross sectional views of the sheet discriminator 100, viewed from a direction indicated by arrow A in FIG. 19. Specifically, FIG. 20A is a cross sectional view illustrating the sheet discriminator 100 when the sheet P is inserted thereto through the opening 102 of the sheet discriminator 100 and FIG. 20B is a cross sectional view illustrating the sheet discriminator 100 when the sheet P is pulled out from the opening 102 of the sheet discriminator 100.

FIG. 21 is a flowchart illustrating an example of control of sheet discrimination performed by the sheet discriminator 100 illustrated in FIG. 19.

The sheet discriminator 100 receives instructions to start the sheet discrimination of the sheet P via the control panel 200 that is mounted on the image forming apparatus 2, as described in step S11 in the flowchart of FIG. 21. After the operation of step S11 in FIG. 21 is completed, the light emission processing unit 130 of the sheet discriminator 100 caused the sheet information detecting sensor 110 to start emitting light, as described in step S12 in the flowchart of FIG. 21. Then, as illustrated in FIG. 20A, the sheet P is inserted toward the end face 103 of the opening 102 of the sheet discriminator 100 in the direction C, as described in step S13 in the flowchart of FIG. 21.

The sheet information detecting sensor 110 performs at least one information detection, i.e., the first information detection(s) D1 in FIG. 20A with respect to the sheet P that is inserted toward the end face 103 of the opening 102. Further, the sheet thickness detecting sensor 170 detects the thickness of the sheet P when the sheet P is inserted toward the end face of the opening 102, as described in step S14 in the flowchart of FIG. 21.

By employing the sheet thickness detecting sensor 170 to detect the thickness of the sheet P as described above, even when a thick paper is used as the sheet P, the thickness of the sheet P can be detected more accurately compared to the case in which the thickness of the sheet P is obtained based on detection results of the transmitted light received by the receiver 160.

After the sheet P has reached the end face 103 of the opening 102, the sheet P is removed. When pulling out the sheet P from the opening 102, the sheet P moves in a direction indicated by arrow D in FIG. 20B. At this time, the sheet information detecting sensor 110 performs at least another one information detection, i.e., the second information detection(s) D2 in FIG. 20B. Accordingly, the sheet information detecting sensor 110 detects the sheet P at different points on the sheet P in the first information detection D1 and the second information detection D2.

As described above, the sheet discriminator 100 according to this example slides the sheet P in the opening 102 for multiple detections. Based on the information obtained by the sheet information detecting sensor 110, the controller 600 discriminates the sheet P, as described in step S15 in FIG. 21.

At this time, by including the detection results obtained by the sheet thickness detecting sensor 170 to the sheet information used to distinguish the sheet P by the controller 600, the sheet P can be discriminated using the information regarding the sheet P having the thickness precisely detected. As a result, the sheet discriminator 100 according to this example can prevent degradation of accuracy of sheet discrimination due to inaccurate detection of the thickness of the sheet P when a thick paper is used as the sheet P.

After the sheet P is removed from the opening 102 and the thickness thereof is not detected by the sheet thickness detecting sensor 170, which is YES in step S16 in FIG. 21, the light emission processing unit 130 causes the sheet information detecting sensor 110 to stop light emission, as described in step S17 in FIG. 21. When the thickness of the sheet P is detected by the sheet thickness detecting sensor 170, which is NO in step S16 in FIG. 21, the procedure is repeated until the thickness of the sheet P is not detected by the sheet thickness detecting sensor 170.

Further, based on detection results regarding the sheet P obtained by the sheet discriminator 100, possible sheet brands, sizes, manufacturers, etc. of the sheet P that is inserted into the sheet discriminator 100 through the opening 102 are displayed on a display of the control panel 200, as described in step S18 of FIG. 21. Then, the controller 600 completes the control of sheet discrimination using the sheet discriminator 100 illustrated in FIGS. 20A and 20B, and sets the image forming conditions according to a correct type of the sheet P out of the listed sheet brands, sizes, and so forth displayed on the control panel 200 to perform image formation.

Further, the sheet discriminator 100 according to this example causes the sheet information detecting sensor 110 to emit light when the control panel 200 indicates to start the sheet discrimination and the sheet information detecting sensor 110 detects information of the sheet P. Accordingly, when compared with a case in which the sheet information detecting sensor 110 constantly emits light, the sheet discriminator 100 according to this example can extend the life span of the sheet information detecting sensor 110 and reduce waste energy consumption thereof.

As described above, in this example, the light source 111 of the sheet information detecting sensor 110 starts light emission when the control panel 200 indicates to start sheet discrimination. However, alternatively, the light source 111 can start light emission when the sheet thickness detecting sensor 170 detects the thickness of the sheet P.

By so doing, compared to a series of operations in which the light source 111 starts light emission, the sheet P is inserted into the opening 102, and the sheet information detecting sensor 110 detects information of the sheet P, a time from the start of light emission to the completion of detection can be shortened. Accordingly, the time of light emission of the sheet information detecting sensor 110 can be shortened, and therefore the sheet discriminator 100 according to this example can extend the life span of the sheet information detecting sensor 110 and reduce waste energy consumption thereof.

Thus, in the sheet discriminator 100 according to this example similar to the sheet discriminator 100 according to the previous example, the controller 600 regulates timing to cause the light source 111 of the sheet information detecting sensor 110 to start or stop light emission based on the detection results obtained by the sheet thickness detecting sensor 170.

Accordingly, the sheet discriminator 100 according to this example can contribute to a reduction in cost when compared with the case in which a sheet detecting sensor to detect whether the sheet P is present or absent at a given position on the sheet loading table 120 is provided to the sheet discriminator 100 to regulate the timing to cause the light source 111 to start or stop light emission based on detection results obtained by the sheet detecting sensor.

It is to be noted that the image forming apparatus 2 included in the image forming system 1 according to this example can be any one of a digital copier, a printer, an offset printer, and other image forming apparatuses.

It is also to be noted that the sheet discriminator 100 mounted on the image forming apparatus 2 can be any one of the sheet discriminators 100 according to the above-described examples of this disclosure.

Next, a description is given of a sheet discriminator 100 according to another example of this disclosure, with reference to FIGS. 22 through 26.

Figure 22:
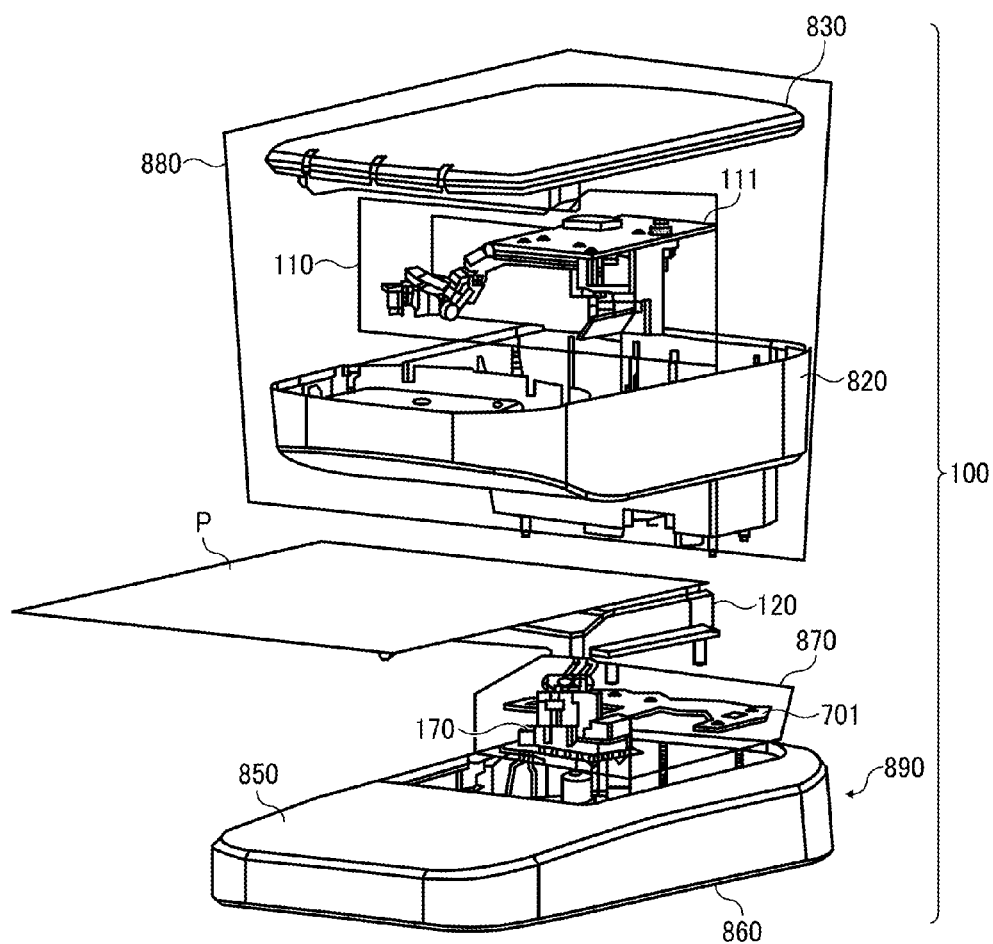
FIG. 22 is an exploded view illustrating a sheet discriminator according to an example of this disclosure.

FIG. 22 is an exploded view illustrating a sheet discriminator 100 according to an example of this disclosure.

The sheet discriminator 100 includes a sheet information detector module 880, a sheet thickness detecting unit 870, the sheet loading table 120, and a base unit 890.

The sheet information detector module 880 functions as a detector body to include the sheet information detecting sensor 110, a case 820, and a cover 830.

The sheet information detecting sensor 110 includes the light source 111. The case 820 holds the sheet information detecting sensor 110 and includes a measuring reference face 901 (see FIG. 23) when measuring the thickness of the sheet P. The cover 830 covers the case 820. The measuring reference face 901 that functions as an opposing member is disposed facing an encoder feeler 704 provided to the sheet thickness detecting sensor 170.

The configuration of the sheet information detecting sensor 110 and detection principle of sheet information performed the sheet information detecting sensor 110 are the same as those described with reference to FIGS. 3 through 10.

The sheet thickness detecting unit 870 includes the sheet thickness detecting sensor 170 and a sensor attaching bracket 701.

The sensor attaching bracket 701 holds the sheet thickness detecting sensor 170.

The sheet thickness detecting sensor 170 is an encoder that functions as a displacement unit to detect an amount of displacement according to thickness of the sheet P.

The configuration of the sheet thickness detecting sensor 170 and detection principle of sheet thickness performed the sheet thickness detecting sensor 170 are the same as those described with reference to FIGS. 11, 12, 13A, and 13B.

The sensor attaching bracket 701 is formed by engineering plastics having excellent rigidity such as ABS (Acrylonitrile-Butadiene-Styrene) resin or by metallic material.

The control of sheet discrimination is the same as those described with reference to FIGS. 2A, 2B, and 11.

The base unit 890 includes a base 860 and a cover 850.

The sheet thickness detecting unit 870 and the sheet loading table 120 to load the sheet P thereon are provided inside the base 860.

The sheet information detector module 880 is supported by the base unit 890.

Figure 23:
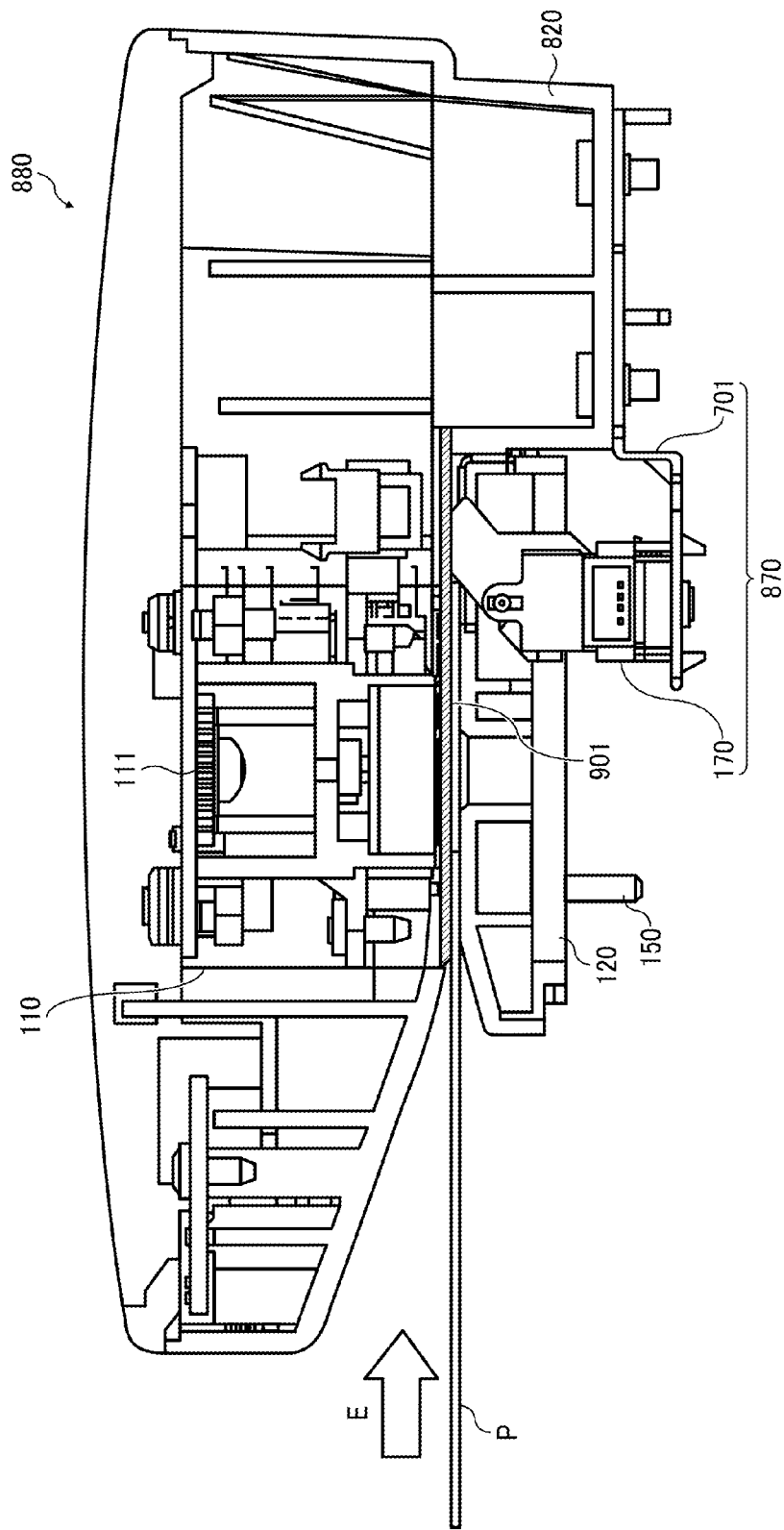
FIG. 23 is a cross sectional view illustrating the sheet discriminator of FIG. 22.

FIG. 23 is a cross sectional view illustrating the sheet discriminator 100 illustrated in FIG. 22. It is to be noted that the base unit 890 is omitted, for convenience.

A side of the sensor attaching bracket 701, which is opposite to another side on which the sheet thickness detecting sensor 170 is mounted, is fixed by a screw or screws to a lower part of the case 820.

In FIG. 23, the sheet P is inserted from a direction indicated by arrow E (hereinafter, a direction E) into a gap formed between the measuring reference face 901 that is a lower face of the case 820 and the sheet loading table 120. The sheet loading table 120 includes the biasing member 150 such as a spring that is attached to a position facing the sheet information detecting sensor 110. Accordingly, the sheet loading table 120 is biased by the biasing member 150 toward the measuring reference face 901. The surface of the sheet P inserted between the measuring reference face 901 and the sheet loading table 120 is pressed against the measuring reference face 901 by the sheet loading table 120.

When the sheet information detecting sensor 110 detects sheet information, the light source 111 emit light toward the surface of the sheet P. Since the surface of the sheet P is pressed onto the measuring reference face 901, the sheet information detecting sensor 110 takes the measuring reference face 901 as a reference face for the measurement of the sheet P.

In the sheet discriminator 100 illustrated in FIG. 23, the sheet thickness detecting sensor 170 is disposed downstream from the sheet information detecting sensor 110 in the sheet inserting direction, which is the direction E. However, the sheet thickness detecting sensor 170 can be disposed upstream from the sheet information detecting sensor 110 in the direction E.

FIG. 24A is a diagram illustrating a state in which the encoder feeler 704 provided to the sheet thickness detecting sensor 170 of the sheet discriminator 100 according to this example before the sheet P is inserted. FIG. 24B is a diagram illustrating a state in which the encoder feeler 704 after the sheet P is inserted. The encoder feeler 704 functions as a displacement gauge.

Figures 25A, 25B:
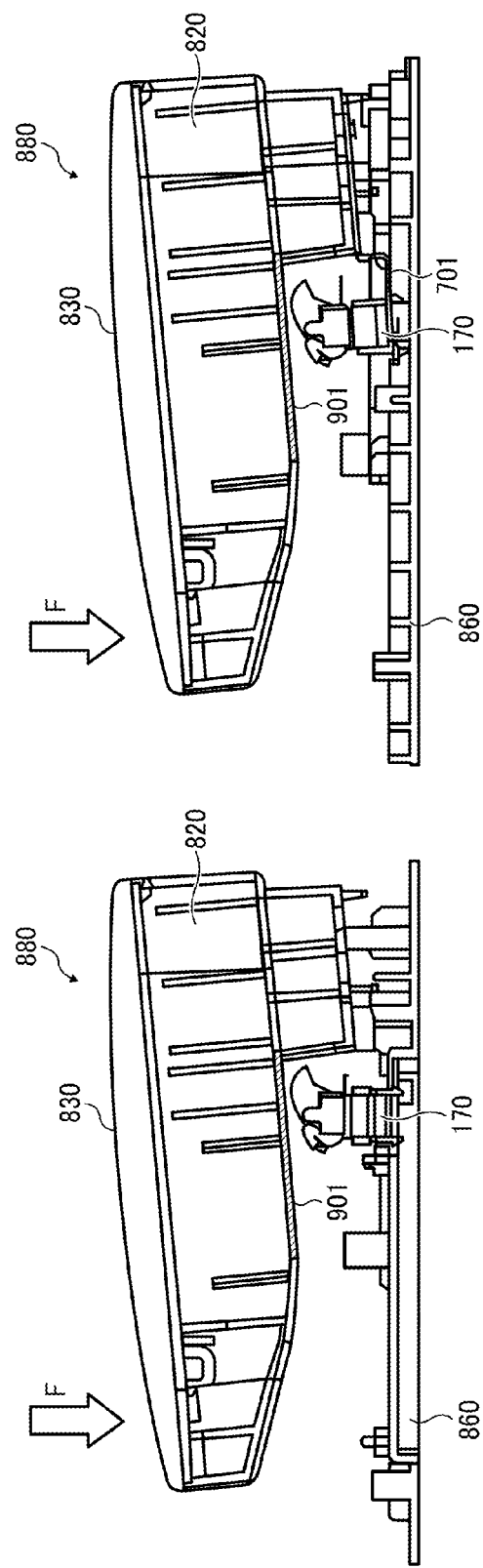
FIG. 25A is a diagram illustrating a positional relation of a measuring reference face and the sheet thickness sensor attached directly to a base when a sheet information detector module of the sheet discriminator is warped.
FIG. 25B is a diagram illustrating a positional relation of the measuring reference face and the sheet thickness sensor attached to the base via a bracket when the sheet information detector module of the sheet discriminator is warped.

In the state before the sheet P is inserted as illustrated in FIG. 24A, the encoder feeler 704 of the sheet thickness detecting sensor 170 is in contact with the measuring reference face 901. When the sheet P is inserted as illustrated in FIG. 25B, the encoder feeler 704 of the sheet thickness detecting sensor 170 contacts the surface of the sheet P to measure the thickness of the sheet P. Since the surface of the sheet P is pressed to the measuring reference face 901, when the sheet thickness detecting sensor 170 detects the thickness of the sheet P, the sheet thickness detecting sensor 170 also takes the measuring reference face 901 as a reference face for the measurement.

The sheet information detector module 880 warps or bends under its own gravity as well as due to a load that is intentionally applied by the hand of an operator placed on an upper part of the sheet information detector module 880.

FIGS. 25A and 25B are diagrams illustrating respective positional relations of the measuring reference face 901 and the sheet thickness detecting sensor 170 when the sheet information detector module 880 of the sheet discriminator 100 is warped or bent by receiving any load.

Specifically, FIG. 25A is a diagram illustrating a comparative example of a positional relation of the measuring reference face 901 and the sheet thickness detecting sensor 170 attached directly to the base 860.

When a load is applied to a point on the sheet information detector module 880 in a direction indicated by arrow F (hereinafter, a direction F) in FIG. 25A, the point of the sheet information detector module 880 inclines downwardly due to the load, and therefore the measuring reference face 901 also inclines downwardly along with the sheet information detector module 880. As the measuring reference face 901 inclines downwardly, the position at which the measuring reference face 901 is formed approaches the sheet thickness detecting sensor 170. Therefore, the thickness of the sheet P is measured thinner by an amount of approach of the measuring reference face 901 to the sheet thickness detecting sensor 170.

The thickness of the sheet P ranges from several tens micrometers [μm] to several hundreds micrometers [μm] and the minimum scanning resolution of the sheet thickness detecting sensor 170 is 5 μm. Accordingly, even small warp or deformation of the sheet information detector module 880 is formed, the effects on measurement of the thickness of the sheet P cannot be ignored.

By contrast, FIG. 25B is a diagram illustrating this example of a positional relation of the measuring reference face 901 and the sheet thickness detecting sensor 170 attached to the base 860 via the sensor attaching bracket 701. As illustrated in FIG. 25B, by attaching the sheet thickness detecting sensor 170 to the sheet information detector module 880 via the sensor attaching bracket 701, even when the measuring reference face 901 inclines downwardly, the sheet thickness detecting sensor 170 inclines downwardly together with the measuring reference face 901. Accordingly, disturbance to the sheet information detector module 880 is restrained to the minimum amount, and therefore sufficient measurement accuracy can be achieved.

Figure 26:
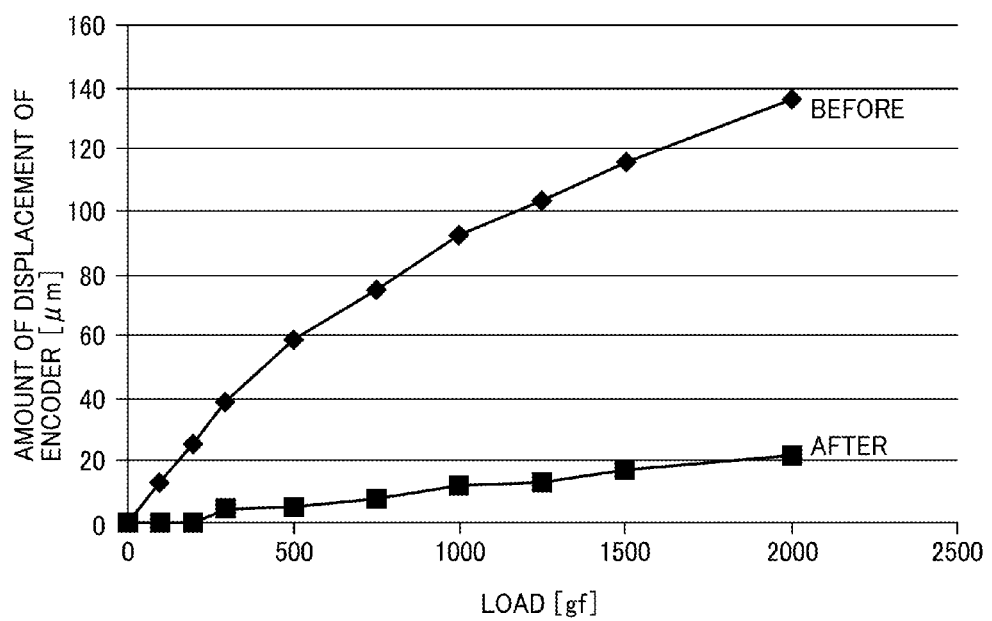
FIG. 26 is a graph showing results of tests regarding effectiveness to prevent misdetection in measurement of sheet thickness when the sheet information detector module of the sheet discriminator is warped intentionally.

FIG. 26 is a graph showing results of tests regarding effectiveness to prevent misdetection in measurement of the thickness of the sheet P when the sheet information detector module 880 of the sheet discriminator 100 is warped intentionally.

The tests were conducted to measure display values of the sheet thickness detecting sensor 170 (i.e., amounts of displacement obtained by the encoder feeler 704) when a load applied in the direction F in FIGS. 25A and 25B at one end of the sheet information detector module 880. It is ideal that the display values obtained by the sheet thickness detecting sensor 170 do not rise even when the load applied to the sheet information detector module 880 is increased.

When the sheet thickness detecting sensor 170 is mounted directly on the base 860, which is "before taking the countermeasure", as the load applied to the sheet information detector module 880 increases, the display values of the sheet thickness detecting sensor 170 also increases significantly. Since the thickness of the sheet P ranges from several tens micrometers [μm] to several hundreds micrometers [μm], the thickness of the sheet P cannot be measured precisely when disturbance was caused "before taking the countermeasure".

By contrast, when the sheet thickness detecting sensor 170 is mounted on the sheet information detector module 880 via the sensor attaching bracket 701, which is "after taking the countermeasure", a rate of an increase in the display values of the sheet thickness detecting sensor 170 to which disturbance is caused can be reduced and restrained to 1/10 to 1/6, compared to an increase in the display values obtained "before taking the countermeasure".

Next, a description is given of the image forming system 1 according to another example of this disclosure.

The schematic configuration of the image forming system 1 according to this example is basically identical to the configuration of the image forming system 1 illustrated in FIG. 16, except for the function of the sheet discriminator 100 provided to the image forming system 1 according to this example.

Specifically, the schematic configuration of the sheet discriminator 100 according to this example is basically identical to the configuration of the sheet discriminator 100 described above with reference to FIGS. 22 and 23. Except, the sheet discriminator 100 according to this example uses the control panel 200 provided to the image forming apparatus 2.

The control panel 200 is provided to the image forming apparatus 2 to function as an indicator to indicate instructions to the sheet discriminator 100 to start sheet discrimination of the sheet P. Specifically, in the previous example, when an image is sequentially formed on multiple sheets of the same type, for example, sheet discrimination of the sheet P starts on insertion of the sheet P into the opening 102 of the sheet discriminator 100 even if the sheet P can be used without sheet discrimination.

By contrast, in this example, sheet discrimination of the sheet P is performed when the control panel 200 provided to the image forming apparatus 2 issues instructions to the sheet discriminator 100 to do so. The other parts and functions are basically identical to the configuration of the sheet discriminator 100 illustrated in FIGS. 20A, 20B, and 21.

The configurations according to the above-described embodiment are examples. The present invention can achieve the following aspects effectively.

Aspect A.

In Aspect A, a sheet discriminator (for example, the sheet discriminator 100) includes an optical information detector (for example, the sheet information detecting sensor 110), the sheet distinguisher (for example, the controller 600), and a sheet thickness detector (for example, the sheet thickness detecting sensor 170). The optical information detector includes a light emitter (for example, the light source 111) to emit light to a surface of a recording medium (for example, the sheet P) and a light receiver (for example, the receivers 113, 114, 115, 118, and 160) to receive the light emitted by the light emitter and to detect information of the recording medium. The sheet distinguisher distinguishes a type of the recording medium based on the information detected by the optical information detector. The sheet thickness detector includes a displacement gauge (for example, the feeler 171 and the encoder feeler 704) and a displacement detector (for example, the optical sensor 172). The displacement gauge sandwiches the recording medium with an opposing member (for example, the bottom face 110a of the sheet information detecting sensor 110, the measuring reference face 901) disposed facing the displacement gauge and moves from an initial position at which the displacement gauge stays when no recording medium is sandwiched with the opposing member. The displacement detector detects an amount of displacement of the displacement gauge. The sheet thickness detector detects a thickness of the recording medium based on detection results obtained by the displacement detector.

In Aspect A, by sandwiching the recording medium between the displacement gauge and the opposing member, the sheet thickness detector can detect the thickness of the recording medium based on an amount of displacement of the displacement gauge physically moved from the initial position according to the thickness of the recording medium. Accordingly, even though the recording medium has a thickness difficult for the optical sheet information detector to precisely detect optically, the sheet thickness detector can detect the thickness of the sheet P accurately. By so doing, the recording medium can be discriminated using information related to the thickness of the recording medium that is detected accurately. As a result, the sheet discriminator can prevent degradation of accuracy of sheet discrimination of the recording medium.

Aspect B.

In Aspect A, the sheet discriminator further includes a light emission controller (for example, the light emission processing unit 130) to control start and stop of the light emitter. When the sheet thickness detector detects the thickness of the recording medium, the light emission controller causes the light emitter to start light emission.

Accordingly, as described in the examples above, the recording medium is inserted into the sheet discriminator, the sheet information detector can start light emission without any operator handling. Consequently, when compared with a case in which the light emission controller does not control light emission of the sheet information detector and the sheet information detector constantly emits light, the life span of the sheet information detector including the light emitter can be extended.

Aspect C.

In Aspect B, when the sheet thickness detector detects no thickness of the recording medium, the light emission controller causes the light emitter to stop light emission.

Accordingly, as described in the examples above, when the recording medium is pulled out from the sheet discriminator, the light emitter of the sheet information detector can stop light emission without any operator handling.

Aspect D.

In Aspect B, when the optical information detector completes detection of information of the recording medium, the light emission controller causes the light emitter to stop light emission.

Accordingly, as described in the examples above, when the recording medium is pulled out from the sheet discriminator, the light emitter of the sheet information detector can stop light emission without any operator handling.

Aspect E.

In any one of Aspects A through D, the light emitter emits laser light.

Accordingly, as described in the examples above, the surface information of the recording medium can be detected more precisely, and therefore more precise detection results can be obtained.

Aspect F.

In any one of Aspects A, B, C, D, and E, the light receiver of the optical information detector includes multiple light receivers. The multiple light receivers includes at least a transmitted light receiver (for example, the receiver 160) to receive transmitted light that is transmitted through the recording medium out of the light emitted from the light emitter.

Accordingly, as described in the examples above, when the thickness of the recording medium is thin, the level of light received by the transmitted light receiver is additionally used as sheet information to obtain the thickness of the recording medium. By so doing, the accuracy of sheet discrimination can be more enhanced.

Aspect G.

In any one of Aspects A through F, the light receiver of the optical information detector includes multiple light receivers. The multiple light receivers include at least a specular reflection light receiver (for example, the receiver 113) to receive specular reflection light emitted from the light emitter and reflected on the recording medium and a diffused reflection light receiver (for example, the receiver 115) to receive diffused reflection light emitted from the light emitter and reflected on the recording medium.

Accordingly, as described in the examples above, the multiple light receivers disposed at different angles can detect scattered light beams of diffused reflection light, and therefore more precise detection results of information can be obtained than the information obtained from specular reflection light alone.

Aspect H.

In any one of Aspects A through G, the sheet discriminator further includes a communicator (for example, the communication cable 60) disposed between the sheet discriminator and an image forming apparatus (for example, the image forming apparatus 2) to communicate with each other.

Accordingly, as described in the examples above, after the sheet discriminator discriminates the information related to the type of the recording medium, the information is sent to the image forming apparatus via the communicator. By so doing, the image forming conditions according to a correct type of the recording medium can be set.

Aspect I.

In any one of Aspects A through H, the sheet discriminator further includes a detector body (for example, the sheet information detector module 880) to include the opposing member and the displacement detector and to maintain a position of the opposing member relative to the displacement detector.

In the sheet discriminator 100, the sheet information detector module 880 that functions as the detector body includes the measuring reference face 901 that functions as the opposing member. When the sheet information detector module 880 receives an external force, a position of the measuring reference face 901 relative to the base unit 890 changes. In a case in which the sheet thickness detecting sensor 170 including the optical sensor 172 that functions as the displacement detector is mounted on the base unit 890, a position of the measuring reference face 901 relative to the sheet thickness detecting sensor 170 also changes. When the sheet thickness detecting sensor 170 measures the thickness of the sheet P, the amount of positional shift or movement of the measuring reference face 901 relative to the sheet thickness detecting sensor 170 is counted as measurement error. By attaching the sheet thickness detecting sensor 170 to the sheet information detector module 880 that includes the measuring reference face 901, regardless of the external force applied to the detector body, sufficient measurement accuracy can be achieved when the sheet thickness detecting sensor 170 detects or measures the thickness of the recording medium.

Aspect J.

In Aspect J, an image forming apparatus (for example, the image forming apparatus 2) includes an apparatus body (for example, the apparatus body 400), an image forming part (for example, the image forming part 420) to form an image on the recording medium, and the sheet discriminator (for example, the sheet discriminator 100) to detect information of the recording medium and discriminate a type of the recording medium. The sheet discriminator of the image forming apparatus is the sheet discriminator according to any one of Aspects A through I and is disposed outside the apparatus body.

Accordingly, as described above, the sheet discriminator can detect the thickness of the recording medium precisely, and therefore can prevent degradation of accuracy of sheet discrimination and can perform image formation under appropriate image forming conditions according to a correct type of the recording medium.

Aspect K.

In Aspect J, the image forming apparatus further includes an indicator (for example, the control panel 200) disposed on the apparatus body and indicating instructions to the light emission controller.

Accordingly, as described in the examples above, an operator inputs instructions via the indicator to cause the sheet information detector to detect information of the recording medium, so that the light emitter can start light emission.

The above-described embodiments are illustrative and do not limit this disclosure. Thus, numerous additional modifications and variations are possible in light of the above teachings. For example, elements at least one of features of different illustrative and exemplary embodiments herein may be combined with each other at least one of substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of this disclosure may be practiced otherwise than as specifically described herein.

What is claimed is:

1. A sheet discriminator, comprising:
    an optical information detector including a light emitter and a light receiver, the light emitter configured to emit light to a surface of a sheet, the light receiver configured to receive the light emitted by the light emitter and reflected by the surface of the sheet, the optical information detector configured to detect information of the sheet based on the received light;
    a sheet distinguisher configured to distinguish a type of the sheet based on the information detected by the optical information detector; and
        a sheet thickness detector including a displacement gauge and a displacement detector, the displacement gauge configured to sandwich the sheet with an opposing member facing the displacement gauge and to move from an initial position at which the displacement gauge stays when no sheet is sandwiched with the opposing member, the displacement detector configured to detect an amount of displacement of the displacement gauge and detect a thickness of the sheet based on detection results obtained by the displacement detector.

2. The sheet discriminator according to claim 1, further comprising:
    a light emission controller configured to control start and stop of the light emitter,
    wherein, when the sheet thickness detector detects the thickness of the sheet, the light emission controller is configured to cause the light emitter to start light emission.

3. The sheet discriminator according to claim 2, wherein, when the sheet thickness detector detects no thickness of the sheet, the light emission controller is configured to cause the light emitter to stop light emission.

4. The sheet discriminator according to claim 3, wherein the light emitter is configured to emit laser light.

5. The sheet discriminator according to claim 3, wherein the light receiver of the optical information detector includes multiple light receivers, the multiple light receivers including at least a transmitted light receiver configured to receive transmitted light transmitted through the sheet out of the light emitted from the light emitter.

6. The sheet discriminator according to claim 3, wherein the light receiver of the optical information detector includes multiple light receivers, the multiple light receivers including at least a specular reflection light receiver and a diffused reflection light receiver, the specular reflection light receiver configured to receive specular reflection light emitted from the light emitter and reflected on the sheet, the diffused reflection light receiver configured to receive diffused reflection light emitted from the light emitter and reflected on the sheet.

7. The sheet discriminator according to claim 3, further comprising:
    a communicator between the sheet discriminator and an image forming apparatus, the communicator configured to communicate with each other.

8. The sheet discriminator according to claim 2, wherein, when the optical information detector completes detection of information of the sheet, the light emission controller is configured to cause the light emitter to stop light emission.

9. The sheet discriminator according to claim 2, wherein the light emitter is configured to emit laser light.

10. The sheet discriminator according to claim 2, wherein the light receiver of the optical information detector includes multiple light receivers, the multiple light receivers including at least a transmitted light receiver configured to receive transmitted light transmitted through the sheet out of the light emitted from the light emitter.

11. The sheet discriminator according to claim 2, wherein the light receiver of the optical information detector includes multiple light receivers, the multiple light receivers including at least a specular reflection light receiver and a diffused reflection light receiver, the specular reflection light receiver configured to receive specular reflection light emitted from the light emitter and reflected on the sheet, the diffused reflection light receiver configured to receive diffused reflection light emitted from the light emitter and reflected on the sheet.

12. The sheet discriminator according to claim 2, further comprising:
    a communicator between the sheet discriminator and an image forming apparatus, the communicator configured to communicate with each other.

13. The sheet discriminator according to claim 2, further comprising:
    a detector body including the opposing member and the displacement detector, the detector body configured to maintain a position of the opposing member relative to the displacement detector.

14. The sheet discriminator according to claim 1, wherein the light emitter is configured to emit laser light.

15. The sheet discriminator according to claim 1, wherein the light receiver of the optical information detector includes multiple light receivers, the multiple light receivers including at least a transmitted light receiver configured to receive transmitted light transmitted through the sheet out of the light emitted from the light emitter.

16. The sheet discriminator according to claim 1, wherein the light receiver of the optical information detector includes multiple light receivers, the multiple light receivers including at least a specular reflection light receiver and a diffused reflection light receiver, the specular reflection light receiver configured to receive specular reflection light emitted from the light emitter and reflected on the sheet, the diffused reflection light receiver configured to receive diffused reflection light emitted from the light emitter and reflected on the sheet.

17. The sheet discriminator according to claim 1, further comprising:
    a communicator between the sheet discriminator and an image forming apparatus, the communicator configured to communicate with each other.

18. The sheet discriminator according to claim 1, further comprising:

a detector body to include the opposing member and the displacement detector, the detector body configured to maintain a position of the opposing member relative to the displacement detector.

19. An image forming apparatus comprising:

an apparatus body;

a sheet discriminator disposed outside the apparatus body, the sheet discriminator including, an optical information detector including a light emitter and a light receiver, the light emitter configured to emit light to a surface of a sheet, the light receiver configured to receive the light emitted by the light emitter and reflected by the surface of the sheet, the optical information detector configured to detect information of the sheet based on the received light, a sheet distinguisher configured to distinguish a type of the sheet based on the information detected by the optical information detector, and a sheet thickness detector including a displacement gauge and a displacement detector, the displacement gauge configured to sandwich the sheet with an opposing member facing the displacement gauge and to move from an initial position at which the displacement gauge stays when no sheet is sandwiched with the opposing member, the displacement detector configured to detect an amount of displacement of the displacement gauge and detect a thickness of the sheet based on detection results obtained by the displacement detector; and an image forming part to form an image on the sheet.

20. The image forming apparatus according to claim 19, further comprising:

an indicator on the apparatus body, the indicator configured to indicate instructions to the light emission controller.

* * * * *